US007176181B2

(12) United States Patent
Zick et al.

(10) Patent No.: US 7,176,181 B2
(45) Date of Patent: Feb. 13, 2007

(54) COMPOSITIONS AND METHODS OF USING GALECTIN-8 AS AN INHIBITOR OF TUMOR CELL GROWTH

(75) Inventors: Yehiel Zick, Carmay Joseph (IL); Yifat Levy, Rehovot (IL); Rinat Arbel-Goren, Rehovot (IL); Denise Ronen, Rehovot (IL); Yaron R. Hadari, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 386 days.

(21) Appl. No.: 10/151,166

(22) Filed: May 21, 2002

(65) Prior Publication Data
US 2003/0220231 A1 Nov. 27, 2003

(51) Int. Cl.
A01N 61/00 (2006.01)
A61K 31/00 (2006.01)
A61K 49/00 (2006.01)
G01N 33/567 (2006.01)
C07K 1/00 (2006.01)

(52) U.S. Cl. .............................. 514/2; 424/9.1; 424/9.2; 436/501; 436/503; 514/1; 530/300; 530/350

(58) Field of Classification Search ................ 530/300, 530/324, 326, 327, 328, 395, 350, 398; 514/2, 514/8, 1, 44; 435/6, 69.1, 91.1, 455, 458; 424/9.1, 9.2; 436/501, 503
See application file for complete search history.

(56) References Cited

U.S. PATENT DOCUMENTS

| 3,687,808 | A | 8/1972 | Merigan et al. |
| 4,469,863 | A | 9/1984 | Ts'O et al. |
| 4,667,025 | A | 5/1987 | Miyoshi et al. |
| 4,762,779 | A | 8/1988 | Snitman |
| 5,034,506 | A | 7/1991 | Summerton et al. |
| 5,278,302 | A | 1/1994 | Caruthers et al. |
| 5,489,677 | A | 2/1996 | Sanghvi et al. |
| 5,525,465 | A | 6/1996 | Haralambidis et al. |
| 5,539,082 | A | 7/1996 | Nielsen et al. |
| 5,587,361 | A | 12/1996 | Cook et al. |
| 5,596,091 | A | 1/1997 | Switzer |
| 5,597,909 | A | 1/1997 | Urdea et al. |
| 5,614,617 | A | 3/1997 | Cook et al. |
| 5,618,704 | A | 4/1997 | Sanghvi et al. |
| 5,627,053 | A | 5/1997 | Usman et al. |
| 5,670,633 | A | 9/1997 | Cook et al. |
| 5,677,439 | A | 10/1997 | Weis et al. |
| 5,681,941 | A | 10/1997 | Cook et al. |
| 5,688,941 | A | 11/1997 | Cook et al. |
| 5,714,331 | A | 2/1998 | Buchardt et al. |
| 5,719,262 | A | 2/1998 | Buchardt et al. |
| 5,869,289 | A | 2/1999 | Hawkins et al. |
| 5,908,761 | A | 6/1999 | Zick |
| 6,228,642 | B1 | 5/2001 | Baker et al. |
| 6,281,333 | B1 | 8/2001 | Hawkins et al. |

FOREIGN PATENT DOCUMENTS

WO WO 99/43857 A1 9/1999

OTHER PUBLICATIONS

R. I. Freshney, Culture of Animal Cells, A Manual of Basic Technique, pp. 3-4 (Alan R. Liss, New York, Publ., 1983).*
G. B. Dermer, Bio/Technology, vol. 12, 1994, pp. 320 (1994).*
Levy, R. et al., J. Biol. Chem., vol. 276, No. 33, pp. 31,285-31,295 (2001).*
Hadari, Y. R. et al., J. cell. Science, vol. 113, pp. 2385-2397 (2000).*
Levy, Y. et al., J. Biol. Chem., vol. 276, No. 33, pp. 31,285-31,295 (2001).*
Andrew Chin, On the preparation and utilization of isolated and purified oligonucleotides, deposited at the Kathrine R. Evern Law Library of the University of North Carolina on Mar. 11, 2002 on CD-ROM.
Barondes et al., Structures and function of a large family of animal lectins, *The Journal of Biological Chemistry*, 269(33)20807-20810 (1994).
Berge et al., Pharmaceutical salts, *Journal of Pharmaceutical Sciences*, 66(1)1-19 (1977).
Camby et al., Galectins are differentially expressed in supratentorial pilocytic astrocytomas, astrocytomas, anaplastic astrocytomas and glioblastomas, and significantly modulate tumor astrocytes migration, *Brain Pathology*, 11:12-26 (2001).
Chonn et al., Recent advances in liposomal drug-delivery systems, *Current Opinion in Biotechnology*, 6:698-708 (1995).

(Continued)

Primary Examiner—Jane Zara
(74) Attorney, Agent, or Firm—Browdy & Neimark, PLLC

(57) ABSTRACT

The present invention provides compositions that enhance or inhibit the interactions of galectin-8 and galectin-8-like proteins with other extracellular matrix proteins or cell surface receptors, and methods for the use thereof as physiological modulators of cell adhesion and in treatment of tumors, both in vivo or ex vivo. It further provides compositions and methods for modulating the expression of galectin-8, and galectin-8-like proteins, particularly to novel antisense oligonucleotides.

5 Claims, 11 Drawing Sheets

OTHER PUBLICATIONS

Englisch et al., Chemically modified oligonucleotides as probes and inhibitors, *Angew. Chem. Int. Ed. Engl.*, 30:613-629 (1991).

Eshhar, Zeilig, Monolonal Antibody Strategy and Techniques., *hybridoma in biotechnology and medicine*, Springer, T. ed., Plenum Press. Chapter 1, pp. 1-41. (1985).

Giancotti et al., Integrin signaling, *Science*, 285:10281032 (1999).

Hadari et al., Galectin-8 binding to integrins inhibits cell adhesion and induces apoptosis, *Journal of Cell Science*, 113:2385-2397 (2000).

Hadari et al., Galectin-8: A new rat lectin, related to galectin-4, *The Journal of Biological Chemistry*, 270(7)3447-3453 (1995).

Hirabayashi et al., Effect of amino acid substitution by site-directed mutagenesis on the carbohydrate recognition and stability of human 14-k-Da β-galactoside-binding lectin, *The Journal of Biological Chemistry*, 266(35)23648-23653 (1991).

Hynes, Cell adhesion: old and new questions, *Trends Cell Biol*, 9:M33-M37 (1999).

Jui et al., Characterization of a hybrid receptor formed by dimerization of the insulin receptor-related receptor (IRR) with the insulin receptor (IR): coexpression of cDNAs encoding human IRR and human IR in NIH-3T3 cells, *Biochemistry*, 35:14326-14330 (1996).

Klapper et al., A subclass of tumor-inhibitory monoclonal antibodies to ErbB-2/HER2 blocks crosstalk with growth factor receptors, *Oncogene*, 14:2099-2109 (1997).

Kroschwitz, J I ed. John Wiley & Sons, Polypeptides, *Concise Encyclopedia of polymer science and engineering*, 858-859 (1990).

Levy et al., Galectin-8 functions an a matricellular modulator of cell adhesion, *The Journal of Biological Chemistry*, 276(33)31285-31295 (2001).

Madsen et al., Cloning, expression, and chromosome mapping of human galectin-7, *The Journal of Biological Chemistry*, 270(11)5823-5829 (1996).

Martin, Ein neuer Zugang zu 2'-O-alkylribonuclosiden und Eigenschaften deren oligonucleotide, *Helvetica Chimica Acta*, 78:486-504 (1995).

Nagy et al., Galectin-8 expression decreases in cancer compared with normal and dysplastic human colon tissue and acts significantly on human colon cancer cell migration as a suppressor, *Gat*, 50:392-401 (2002).

Neugebauer et al., Cell-surface regulation of $\beta_1$-integrin activity on developing retinal neurons, *Nature*, 350:68-71 (1991).

Nielsen et al., Sequence-selective recognition of DNA by strand displacement with a thymine-substituted polyamide, *Science*, 254(5037)1497-1500 (1991).

Paz et al., Phosphorylation of insulin receptor substrate-1 (IRS-1) by protein kinase B positively regulates IRS-1 function, *The Journal of Biological Chemistry*, 274(40)28816-28822 (1999).

Raz et al, Differential expression of endogenous lectins on the surface of nontumorigenic, tumorigenic, and metastatic cells, *Cancer Res*, 46:3667-3672 (1986).

Raz et al., Evidence for the role of 34-kDa galactoside-binding lectin in transformation and metastasis, *Int. J. Cancer*, 46:871-877 (1990).

Sanghvi, et al., *Antisense Research and Applications*, CRC Press, Boca Raton. Chapter 15: 276-278. (1993).

Sanghvi, et al., *Antisense Research and Applications*, CRC Press, Boca Raton. Chapter 16: 289-302. (1993).

Sharon et al., Lectins-proteins with a sweet tooth: functions in cell recognition, *Essays Biochem.*, 30:59-75 (1995).

Su, Zao-Zhong et al., Surface-epitope masking and expression cloning identifies the human prostate carcinoma tumor antigen gene PCTA-1 a member of the galectin gene family, *Proc. Natl. Acad. Sci. USA*, 93:7252-7257 (1996).

Tracey et al., Subunit molecular mass assignment of 14,654 Da to the soluble β-galactoside-binding lectin from bovine heart muscle and demonstration of intramolecular disulfide bonding associated with oxidative inactivation, *The Journal of Biological Chemistry*, 267(15)10342-10347 (1992).

\* cited by examiner

```
   1  AATTCCCCCCCTGGC TGGGGACAAGTTA TTACT TTGAGTAATCCTTAAA TGAAGAGTGGG  60
  61  TAAAGCCCAT ATACGG AAGAGAGACTCCAGTCAACAATATCAA TAAGTTG AAGAAGA AA A  120
 121  ATGTTGTCC TTAAGC AATC TACAAAATA TCATCTATAACCCGACAATCCCC TATG TCAG T  180
      Met Leu Ser Leu Ser Asn Leu Gln Asn Ile Ile Tyr Asn Pro Thr Ile Pro Tyr Val Ser
 181  ACCA TTACTGAGCAGTTGAAGCCTGGCTCTTTGATCGTGATCCGTGGCCATGTT CC TAA A  240
      Thr Ile Thr Glu Gln Leu Lys Pro Gly Ser Leu Ile Val Ile Arg Gly His Val Pro Lys
 241  GAT TCAGAAAGATTCCAAGTAGACTTTCAGCATGGCAACAGCCTGAAGCCGAGAGCT GAT  300
      Asp Ser Glu Arg Phe Gln Val Asp Phe Gln His Gly Asn Ser Leu Lys Pro Arg Ala Asp
 301  GTGGCCTTCCAC TTTAACCCTCGCTTCAAAAGGTCCAACTGC ATTGTTTGTAAC ACACTG  360
      Val Ala Phe His Phe Asn Pro Arg Phe Lys Arg Ser Asn Cys Ile Val Cys Asn Thr Leu
 361  ACAAATGAGAAATGGGGCTGGGAGGAGATCACCCACGACATGCCTTTCAGAAAAGAAAAG  420
      Thr Asn Glu Lys Trp Gly Trp Glu Glu Ile Thr His Asp Met Pro Phe Arg Lys Glu Lys
 421  TCCTTTGAG ATTGTGATCATG GTGCTAAAGAACAAA TTCCACGTGGCTGTGAATGGAAAG  480
      Ser Phe Glu Ile Val Ile Met Val Leu Lys Asn Lys Phe His Val Ala Val Asn Gly Lys
 481  CACATTCTGCTG TATGCCCACAGGATCAACCCAGAGAAGATAGACACACTGGGCATCTTC  540
      His Ile Leu Leu Tyr Ala His Arg Ile Asn Pro Glu Lys Ile Asp Thr Leu Gly Ile Phe
 541  GGCAAAGTGAACATTCAC TCCATCGGGTTCAGATTCAGCTCGGATTTA CAGAGTATGGAA  600
      Gly Lys Val Asn Ile His Ser Ile Gly Phe Arg Phe Ser Ser Asp Leu Gln Ser Met Glu
 601  ACA TCTACTCTGGGACTGACACAG ATAAGTAAAGAAAATATACAAAAGTCTGGCAAGCTC  660
      Thr Ser Thr Leu Gly Leu Thr Gln Ile Ser Lys Glu Asn Ile Gln Lys Ser Gly Lys Leu
 661  CAT TTGAGCCTGCCATTTGAAGCAAGGTTGAATGCCTCCATGGGCCCTGGACGAACCGTT  720
      His Leu Ser Leu Pro Phe Glu Ala Arg Leu Asn Ala Ser Met Gly Pro Gly Arg Thr Val
 721  GTC GTTAAAGGAGAAGTGAATACA AATGCCACAAGCTTTAATGTTGACCTAGTGGCAGGA  780
      Val Val Lys Gly Glu Val Asn Thr Asn Ala Thr Ser Phe Asn Val Asp Leu Val Ala Gly
 781  AGGTCAAGGGATATC GCTCTGCACTTGAACCCACGCCTGAATGTGAAAGCGTTTGTAAGA  840
      Arg Ser Arg Asp Ile Ala Leu His Leu Asn Pro Arg Leu Asn Val Lys Ala Phe Val Arg
 841  AACTCC TTTCTTCAGGAT GCCTGGGGAGAAGAGGAGAGAAACATTACCTGCTTCCCATTT  900
      Asn Ser Phe Leu Gln Asp Ala Trp Gly Glu Glu Glu Arg Asn Ile Thr Cys Phe ProPhe
 901  AGT TCTGGGATGTACTTT GAGATGATA ATT TACTGTGATGTCCGAGAGTTCAAGGTTGCA  960
      Ser Ser Gly Met Tyr Phe Glu Met Ile Ile Tyr Cys Asp Val Arg Glu Phe Lys Val Ala
 961  GTAAATGGTGTGCACAGCCTGGAGTACAAGCACAGATTTAAAGAC CTAAGCAGCATCGAC  1020
      Val Asn Gly Val His Ser Leu Glu Tyr Lys His Arg Phe Lys Asp Leu Ser Ser Ile Asp
1021  ACACTAGCAGTTGAT GGCGATATCCGTTTGCTGGATGTAAGGAGCTGGTAGCTATCATGA  1080
      Thr Leu Ala Val Asp Gly Asp Ile Arg Leu Leu Asp Val Arg Ser Trp ***
1081  CTGCCAGAACC CTG GAAATACAAAATGGCTTATCCGATACTGGCCATGTCAAATGCATCT  1140
1141  CGC TTTCACCACAT TGTTATACTGTTAAGTTGAGCTCGCACAACATCAAGTCCTACTGGT  1200
1201  GTT GTCAGGCCTGGCCATGCAGTGTGGCTACCTCTGAATTCCCAGGA  1247
```

COMPOSITIONS AND METHODS OF USING GALECTIN-8 AS AN INHIBITOR OF TUMOR CELL GROWTH

FIELD OF THE INVENTION

The present invention relates to compositions that enhance or inhibit the interactions of galectin-8 and galectin-8-like proteins with other extracellular matrix proteins or cell surface receptors, to the use thereof as physiological modulators of cell adhesion and in treatment of tumors, either in vivo or ex vivo. It further relates to compositions and methods for modulating the expression of galectin-8, and galectin-8-like proteins, particularly to novel antisense oligonucleotides.

BACKGROUND OF THE INVENTION

Extracellular matrix (ECM) proteins have an important function in providing structural integrity to tissues and in presenting proper environmental cues for cell adhesion, migration, growth, and differentiation. All of these aspects rely on the spatiotemporal expression of adhesive as well as anti-adhesive components in extracellular matrices and on the cell surface. These include "classical" ECM proteins like fibronectin and laminin that act as anti adhesive ligands under certain experimental conditions. Many proteins that inhibit cell adhesion were classified as matricellular proteins. This group embodies proteins such as thrombospondin, tenascin, and hevin that do not serve as integral components of matrix elements but rather function through binding to matrix proteins as well as to cell surface receptors. Cell-matrix interactions depend to a large extent upon the engagement of specific ECM proteins with cell surface integrins (Hynes R O 1999 *Trends Cell Biol* 9:M33–M37; Giancotti F G & Ruoslahti E 1999 *Science* 285:1028–1032). Cell adhesion also depends upon carbohydrate-protein interactions, mediated by mammalian lectins of different families (Sharon N & Lis H 1995 *Essays Biochem* 30:59–75).

Lectins are proteins that are defined by their ability to bind carbohydrates specifically and to agglutinate cells. Lectins have been shown to be involved in a wide variety of cellular functions including cell-cell and cell-matrix interactions. Lectins are widespread among plants, invertebrates and mammals.

Animal lectins have been grouped into four distinct families: C-type lectins, which include selectins; P-type lectins; galectins (formerly termed S-type lectins or S-Lac lectins); and pentraxins (Barondes S H et al. 1994 *J Biol Chem* 269:20807–20810).

Galectins require fulfillment of two criteria: affinity for β-galactosides and significant sequence similarity in the carbohydrate recognition domain (CRD) (Hirabayashi J & Kasai K 1991 *J Biol Chem* 266:23648–23653). Galectin-1 and -2 are homodimers with subunit molecular weight of ~14 kDa, that are not subjected to post-translational modifications (Tracey B M et al. 1992 *J Biol Chem* 267:10342–10347). Galectin-1 and galectin-3 are the best characterized of the mammalian galectins. Galectin-1 is found in the extracellular matrix aid has been shown to interact with laminin. It is known to both promote and inhibit cell adhesion. In skeletal muscle, galectin-1 inhibits cell matrix interaction and is thought to play a role in muscle development while in other cell types galectin-1 promotes cell-matrix adhesion. Galectin-1 has also been implicated in the regulation of cell proliferation and in some immune functions. Over-expression of galectin-1 has been also shown to correlate with tumor metastasis potential (Raz A et al 1986 *Cancer Res* 46:3667–3672).

Galectin-3 is a monomeric protein, composed of an N-terminal half made of tandem repeats characteristic of the collagen superfamily, and a C-terminal half homologous to galectin-1 and -2. Like galectin-1, galectin-3 binds to laminin. It is known to plays a role in inflammation by binding to both IgE and IgE receptor thereby causing activation of mast cells and basophils. Galectin-3 has been shown to concentrate in the nucleus of certain cell types during proliferation. Expression of galectin-3 is elevated in certain tumors, suggesting that galectin-3 plays a role in metastasis. Indeed overexpression of galectin-3 in a weakly metastatic cell line caused a significant increase in metastatic potential (Raz A et al 1990 *Int J Cancer* 46:871–877).

Galectin-4 was cloned from rat intestine, and a homologous protein was cloned from nematode. Galectin-4 is a monomer with molecular mass of 36 kDa. It contains tandem domains of ~140 amino acid each, homologous to galectin-1 and -2, that are separated by a link region. The function of galectin-4 is presently unknown.

The expression of human galectin-7 appears to be limited to keratinocytes. Galectin-7 is though to play a role in cell-matrix and cell-cell interactions as galectin-7 is sharply downregulated in anchorage independent keratinocytes and is absent in malignant keratinocytes cell lines. Galectin-7 may be required for the maintenance of normal keratinocytes (Madsen P et al *J Biol Chem* 270:5823–5829).

One of the present inventors has previously disclosed (U.S. Pat. No. 5,908,761) rat galectin-8, which is a 34-kDa secreted protein expressed in a wide variety of tissues in adult rats including lung, liver, kidney, spleen and cardiac and skeletal muscles. This disclosure is incorporated herein in its entirety by reference. Galectin-8 is composed of two homologous (38% identity) carbohydrate recognition domains joint by a short (~26 amino acids) linking peptide. The link region of rat galectin-8 is not similar to either the link region of galectin-4 or to the proline, glycine and tyrosine-rich repeat domain of galectin-3.

Galectin-8 is a secreted protein, although lacking a signal peptide. Trypsinization experiments have shown that a significant fraction of the secreted galectin-8 remains bound to the extracellular surface. Galectin-8 form tight complexes with a selective subset of integrins, and secreted, soluble galectin-8 was shown to specifically inhibit cell adhesion. Over-expression of galectin-8 in 1299 cells, a cell line derived from human non-small cell lung carcinoma, significantly promoted inhibition of cell adhesion. However, full-length antisense galectin-8 showed no effect on the adhesion of these cells (Hadari Y R et al 2000 *J Cell Sci* 113:2385–2397).

Human galectin-8 has also been cloned (U.S. Pat. Nos. 5,869,289; 6,281,333), and was shown to share features with rat galectin-8 as well as other mammalian galectins, which are involved in the regulation of cell growth and development, including metastatic potential. WO99/43857 discloses that prostate carcinoma tumor antigen-1 (PCT-1), the human isoform of galectin-8, is highly expressed in certain forms of prostate carcinomas (Su Z-Z et al 1996 *Proc Natl Acad Sci U.S.A.* 93:7252–7257). Galectin-8 is over-expressed in lung carcinomas and is also overexpressed in the invasive regions of xenografted glioblastomas (Camby I et al 2001 *Brain Pathol* 11:12–26). In contrast, galectin-8 expression decreased in colon cancer compared with normal human colon tissue (Nagy et al 2002 *Gut* 50:392–401.

The diagnostic utility of human galectin-8 was proposed (U.S. Pat. No. 6,281,333), and PCT antigen-1 (WO99/

43857) has been disclosed as useful for the detection of metastatic cancer cells. However, WO99/43857 fails to teach the differences in galectin-8 expression in various tumor types, and thus provides no guidance for distinguishing malignant cancers from benign hyperproliferative disorders, thus rendering the claimed diagnostic method unreliable.

Preliminary in vitro results of the present inventors and coworkers (Levy Y et al 2001 *J Biol Chem* 276:31285–31295) have shown galectin-8 as a physiological modulator of cell adhesion, capable of both promoting and inhibiting cell adhesion depending on its configuration.

Cell adhesion is critical to the development and survival of multicellular organisms. The process of cell adhesion is complex, requiring participation of extracellular proteins such as fibronectin, vitronectin, collagen, laminin and galectin and numerous families of cellular receptors such as the integrins and cellular adhesion molecules (CAMS). These molecules are involved in the adhesion of both normal and malignant cells, and therefore are crucial to neoplastic proliferation and metastasis.

In view of the accumulated information described above, ECM proteins and matricellular proteins such as galectins are assumed to play a role in modulating cell-matrix interactions in a variety of pathological processes, including tumor development. However, the therapeutic utility of galectins in general, and galectin-8 in particular, were never actually reduced to practice for treatment of cell-proliferative pathological disorders.

Thus, there is a recognized need for, and it would be highly advantageous to have methods of regulating expression or function of galectin-8 and galectin-8 like proteins and using same as a means for modulating cell interactions in vivo. More particularly, there is an unmet need for method of using these proteins as a means of inhibiting tumor cell growth.

SUMMARY OF THE INVENTION

It is an object of the present invention to provide methods employing novel matricellular protein interactions to modulate cell growth, more particularly to provide methods of using galectin-8 and galectin-8 like proteins as physiological modulators of cell adhesion. It is a further object of the present invention to provide methods of using galectin-8 and galectin-8 like proteins and oligonucleotide molecules encoding same for treating pathological disorders relating to abnormal cell growth. It is yet a further object of the present invention to provide methods of therapeutically intervening in proliferative disorders, particularly in cancer, by modulating the expression or function of galectin-8.

The present invention discloses compositions and methods for enhancing or inhibiting the interactions of galectin-8 and galectin-8-like proteins with other extracellular matrix proteins or cell surface receptors, and methods for use thereof as physiological modulators of cell adhesion and in treatment of tumors, both in vivo or ex vivo. It further discloses compositions and methods for modulating the expression of galectin-8, and galectin-8-like proteins, particularly to novel antisense oligonucleotides.

The present invention is based in part on certain recently discovered matricellular protein interactions, specifically to interactions of galectin-8 and galectin-8 like proteins with different cell types. The present invention relates to the function of immobilized galectin-8 as a matrix protein promoting cell adhesion by ligation to and clustering sugar moieties of cell surface integrin receptors. The present invention discloses the use of these interactions for in vivo or ex-vivo treatment of proliferative cell disorders.

It is now disclosed for the first time that exposure to compositions comprising soluble galectin-8 inhibits tumor progression in vivo. By way of non-limiting example, tumor explants pretreated with soluble galectin-8 in vitro showed significantly reduced tumor growth when subsequently transplanted into host animals.

In one aspect the present invention discloses compositions and methods for inhibiting cell adhesion mediated by immobilized (or, cell-bound) galectin-8, wherein inhibition may be achieved by specific or non-specific modulators, including but not restricted to the group consisting of EDTA, serum proteins, anti-β1 integrin antibodies, anti-galectin-8 antibodies and soluble galectin-8 and galectin-8 like proteins.

In another aspect the present invention provides compositions and methods for treating pathological disorders relating to abnormal cell growth. In preferred embodiments, the present invention relates to pathological disorders wherein the pathological cells are tumor cells. Tumors amenable to treatment according to the principles of the invention include but are not limited to lung, liver, brain, bladder, melanoma and prostate cancers.

According to more preferred embodiments, the present invention relates to treatment of tumor cells over-expressing galactin-8 and galectin-8 like proteins.

According to a currently most preferred embodiment the present invention relates to treatment of prostate tumors.

In one aspect of the present invention the method of treating pathological disorders relating to abnormal cell growth comprises administering to a subject in need thereof a therapeutically effective amount of a composition that inhibits cell adhesion mediated by immobilized galectin-8 or galectin-8 like proteins. In the context of physiologically relevant interactions, cell adhesion mediated by immobilized galectin-8 may be equated to cell adhesion mediated by cell-surface bound galectin-8.

In preferred embodiments, the inhibiting composition comprises soluble galectin-8 or galectin-8 like proteins or fragments thereof selected from:

a. the protein galectin-8 having the amino acid sequence shown in FIG. 1 (SEQ ID NO:2) or its human homolog shown in FIG. 2 (SEQ ID NO:4);

b. a protein having greater than 80 percent homology to all or part of the amino acid sequence of SEQ. ID NO:2 or SEQ ID NO:4;

c. a protein of (a) or (b) in which one or more amino acid residues have been added, deleted, replaced or chemically modified without substantially affecting the biological activity of the protein;

d. a biologically active fragment of any one of (a–c);

e. a homologous polypeptide to that of any one of (a–d) derived from another mammal and which has a similar biological activity of that of (a) or (b) or (c) or (d).

It is now disclosed for the first time that exposure to compositions comprising soluble galectin-8 inhibits tumor progression in vivo. By way of non-limiting example, tumor explants pretreated with soluble galectin-8 in vitro developed less well when subsequently transplanted into host animals.

In other preferred embodiments, the inhibiting composition is selected from, but not restricted to the group consisting of anti-galectin-8 antibodies and anti-β1 integrin antibodies. In one currently most preferred embodiment antibodies to galectin-8 are directed to an epitope that is specific to this particular lectin, exemplified by but not limited to antibodies to the hinge region that links the two carbohydrate recognition domains. While antibodies to the hinge region are known (U.S. Pat. No. 5,908,671), their utility in vivo for modulating cell growth, particularly abnormal cell growth, was not reduced to practice.

In another aspect the present invention provides a method for treating pathological disorders relating to abnormal cell growth comprising the step of administering to a subject in need thereof a therapeutically effective amount of a composition inhibiting the expression of galectin-8 and/or galectin-8 like proteins.

The present invention discloses antisense compounds, particularly oligonucleotides, for use in modulating the function of nucleic acid molecules encoding galectin-8, ultimately modulating the amount of galectin-8 produced. This is accomplished by providing oligonucleotides that specifically hybridize with nucleic acids encoding galectin-8.

In more preferred embodiments, the compositions inhibiting the expression of galectin-8 and galectin-8 like proteins comprise an antisense oligonucleotide, wherein said oligonucleotide comprises a contiguous nucleotide sequence selected from the group consisting of:

a. an oligonucleotide complementary to a portion of the nucleotide sequence of FIG. 1 (SEQ ID NO:1) or the human homolog of SEQ ID NO:3 (FIG. 2);

b. an oligonucleotide having the nucleic acid sequence of (a) in which one or more codons has been added, replaced or deleted in a manner that the sequence essentially retains the same biological properties as the unaltered sequence;

c. an oligonucleotide having a nucleotide sequence, which is homologous to the molecule of (a) or (b), having a similar biological activity to that of the sequences of (a) or (b);

d. a fragment of the nucleotide sequences of any one of (a–c) which essentially retains the biological activity of the unfragmented molecule;

e. an oligonucleotide molecule comprising the sequence of a fragment of any one of (a–d) and additional nucleotide sequences in the 3' and 5' ends; and f. an oligonucleotide according to any one of (a–e) containing modified backbone or non-natural internucleotide linkage.

One currently most preferred embodiment comprises antisense oligonucleotides hybridizing to the sequences encoding the "hinge region" of galectin-8. These most preferred embodiments will be complementary to all or part of the coding sequence for amino acids 152–182 of hGalectin-8 (designated herein as SEQ ID NO:5), namely:

```
TTT AGC TTC AGC TCG GAC TTA CAA AGT ACC CAA GCA

TCT AGT CTG GAA CTG ACA GAG ATA AGT AGA GAA AAT

GTT CCA AAG TCT GGC ACG
```

Clearly it is possible to use other oligonucleotide sequences, from other parts of the molecule, if they prove to inhibit specifically the expression of galectin-8.

Currently preferred embodiments comprise an oligonucleotide of 5 to 50 nucleotides in length, more preferably 10–40 nucleotides in length, most preferably 15–30 nucleotides in length.

Nucleotide constructs comprising the antisense oligonucleotide sequences of the invention, and vectors comprising these constructs are also explicitly encompassed within the scope of the invention.

The antisense oligonucleotides of the invention are administered to a subject in need thereof in vivo, by methods well known in the art, though ex-vivo treatment may also be useful in the treatment of certain diseases or disorders.

BRIEF DESCRIPTION OF THE DRAWINGS

FIG. 1 cDNA sequence (SEQ ID NO:1) of galectin-8 and deduced protein sequence (SEQ ID NO:2).

Figure 2:
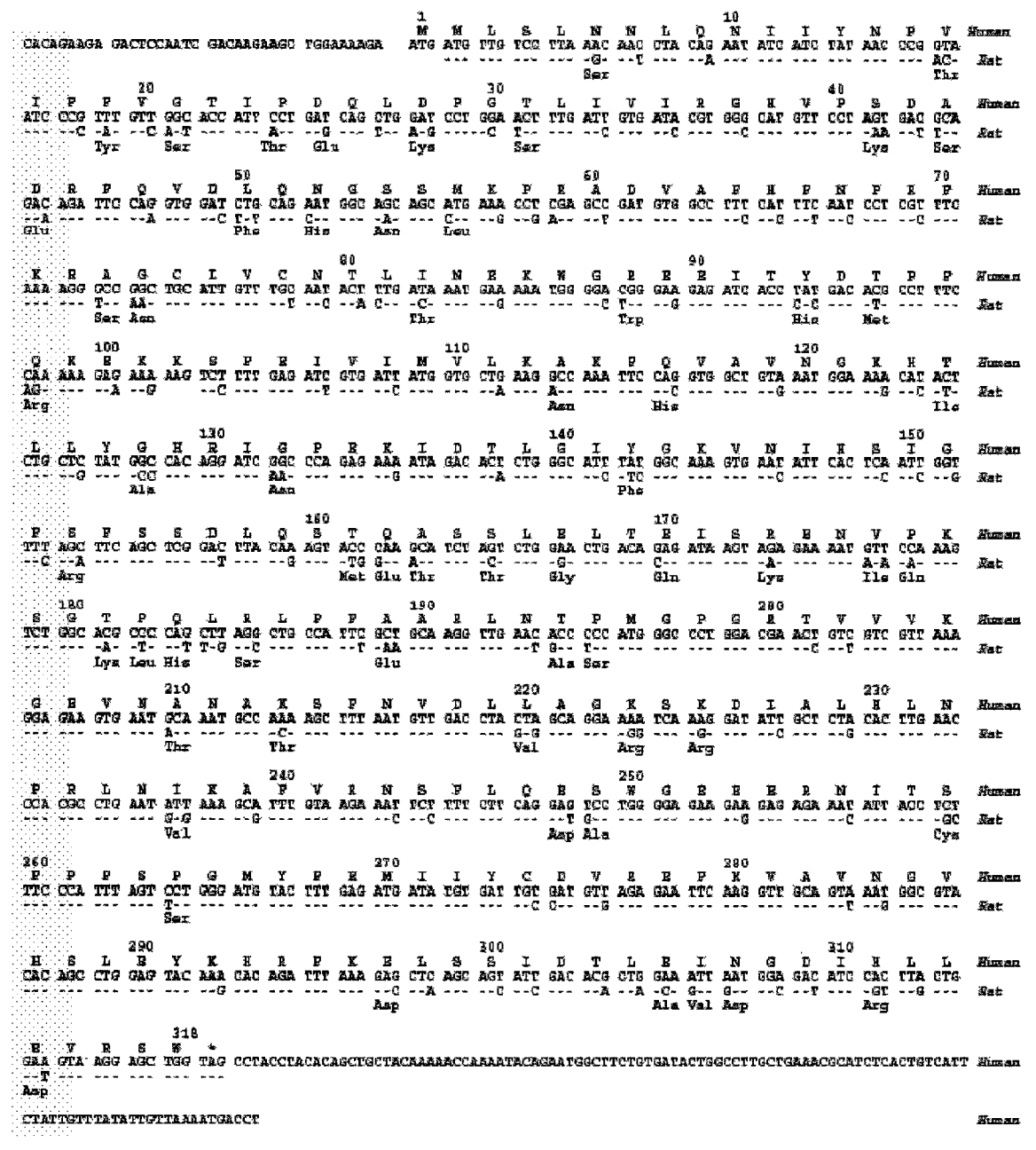

FIG. 2 Comparison of human cDNA sequence (SEQ ID NO:3) of galectin-8 and its deduced protein sequence (SEQ ID NO:4) to the sequence of rat galectin-8.

DETAILED DESCRIPTION OF THE INVENTION

Figure 3:
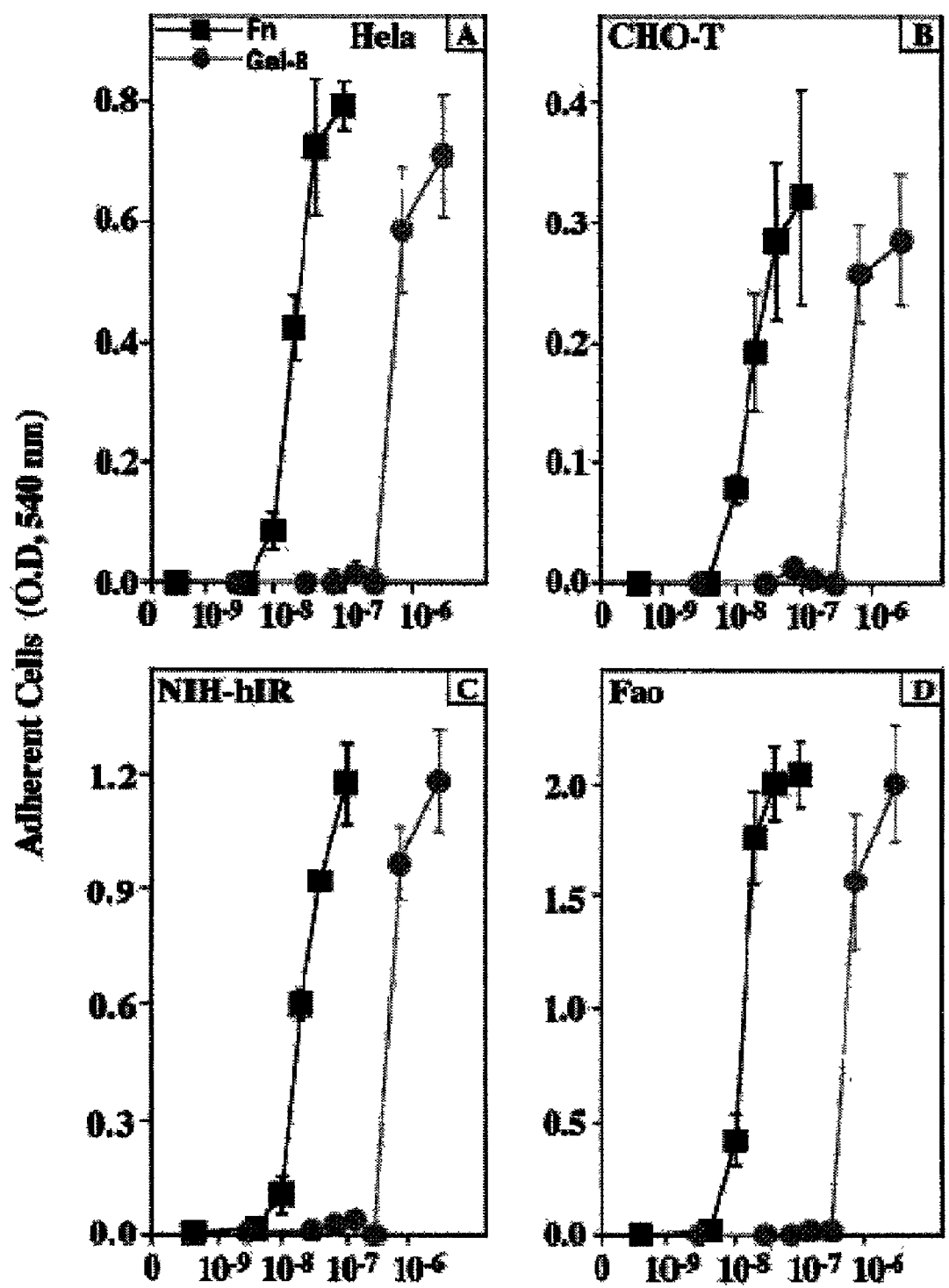
FIG. 3 Cell adhesion to plates coated with galectin-8 or fibronectin. Plates were precoated with the indicated concentration of galectin (●) or fibronectin (■) and the adhesion of HeLa (A), CHO-T (B), NIH-hIR (C) and Fao (D) cells was measured.

The role of galectins in cell adhesion has been studied for some time and the possible utility of these molecules for treatment of hyperproliferative disorders has been proposed, however, the present invention discloses for the first time the successful use of galectin-8 for the treatment of cancer.

The background art has disclosed analysis and detection methods of galectins in tumors, focusing mainly on galectin-1 and galectin-3. Expression of galectin-8 was found to be tumor-dependent, over-expressed in certain cancer types while down regulated in others, and diagnostic methods using galectin-8 have been disclosed, though the reliability of these methods remains equivocal. As disclosed herein, galectin-8 is a modulator of cell adhesion, which is capable of both promoting and inhibiting cell adhesion depending on the configuration and context in which it is present. The novel matricellular galectin-8 interactions elaborated by the present invention are employed herein for therapeutically intervening in proliferative disorders, particularly in cancer.

The present invention discloses compositions and methods for using galectin-8 or specific inhibitors of galectin-8 to beneficially regulate cell-cell and cell-matrix interactions. Depending on the context of the disorder or disease to be treated these compositions and methods may be used to increase cell adhesion, for example in order to prevent or reduce cellular motility, for instance in order to diminish migration of metastatic cancer cells. In alternative applications the condition to be treated may benefit from enhanced cell motility, for instance in order to enhance or expedite processes of wound healing, by modifying the migration of cells into the wound area.

The mechanism of action of the compositions according to the present invention may be direct, e.g., by preventing or promoting binding of cell surface galectin-8 to other cell surface proteins or matrix receptors, or by preventing or promoting binding of soluble galectin-8 to its potential receptors.

The mechanism of action of galectin-8 in modulating cell adhesion may also be indirect, e.g., by interfering or promoting activity of genes that are regulated by galectin-8.

In this regard it is noteworthy that the present inventors have implicated certain galectin reactive genes as the underlying cause of enhanced metastatic potential in cancers over-expressing galectin-8. By way of a non-limiting example, many prostate cancers over-express galectin-8, and these often metastasize to sites in the bone. Microarrays used to identify galectin responsive genes have now shown that osteoclast stimulation factor is one of the galectin-8 reactive genes, thus providing a basis for explaining the prevalence of bone metastases in these tumors.

Irrespective of the underlying mechanism, it appears that over-expression of galectin provides an advantage to the tumorigenic potential of malignantly transformed cells. Therefore, the compositions and novel methods of using these compositions in vivo will have therapeutic utility in all tumors that over-express galectin-8 compared to normal levels in surrounding healthy tissue.

Determination of whether a particular tumor is amenable to treatment may be carried out by a simple diagnostic test. Identification of the level of expression of galectin-8 or galectin-8 like protein is readily accomplished by biopsy or possibly even a simple blood test.

As used herein, "galectin-8" refers to a protein having the amino acid sequence shown in FIG. 1 (SEQ ID NO:2), or its homolog obtained from any species, particularly mammalian, preferably rat or human, from any source whether natural, synthetic, semi-synthetic or recombinant.

As used herein, "galectin-8 like" protein refers to a biologically active S-type lectin, having greater than 80 percent homology to all or part of the amino acid sequence shown in FIG. 1 (SEQ ID NO:2), or it homolog obtained from any species, particularly mammalian, preferably rat or human, from any source whether natural, synthetic, semi-synthetic or recombinant.

As used herein, "soluble" galectin-8 and galectin-8 like protein refer to non-immobilized proteins.

The present invention relates to matricellular protein interactions, more specifically to galectin-8 and galectin-8 like proteins as physiological modulators of cell adhesion.

Thus, the present invention relates to compositions for modulating cell adhesion comprising galectin-8, or galectin-8 like proteins and fragment thereof selected from:

a. the protein galectin-8 having the amino acid sequence shown in FIG. 1 (SEQ ID NO:2) or its human homolog shown in FIG. 2 (SEQ ID NO:4);

b. a protein having greater than 80 percent homology to all or part of the amino acid sequence of SEQ ID NO:2 or SEQ ID NO:4;

c. a protein of (a) or (b) in which one or more amino acid residues have been added, deleted, replaced or chemically modified without substantially affecting the biological activity of the protein;

d. a biological active fragment of any one of (a–c);

e. an homologous polypeptide to that of any one of (a–d) from another mammal and which has a similar biological activity of that of (a) or (b) or (c) or (d);

further comprising a pharmaceutically acceptable diluent or carrier.

In one preferred embodiment, the present invention relates to compositions as disclosed in U.S. Pat. No. 5,908,761 for modulating cell adhesion comprising galectin-8 or galectin-8 like proteins or fragment thereof selected from:

a. the protein galectin-8 having the amino acid sequence shown in FIG. 1 (SEQ ID NO:2);

b. a protein other that the protein of (a), extracted from a mammal of a species other than rat and which has sugar-binding ability and the ability to agglutinate formaldehyde-fixed, trypsin-treated rabbit erythrocyte, which protein is encoded by DNA which hybridizes to the DNA of SEQ ID NO:1 under moderately stringent conditions carried out at 42° C. in 50% formamide 5×SSC with washes at 60° C. in 0.1×SSC, 0.1% SDS;

c. a protein other that the protein of (a), extracted from a mammal of a species other than rat and which has sugar-binding ability and the ability to agglutinate formaldehyde-fixed, trypsin-treated rabbit erythrocyte, which protein is bound by an antibody specific for an epitope in the region of amino acids 153–184 of SEQ ID NO:2; and d. a fragment of (a), (b), or (c) which has sugar-binding ability and the ability to agglutinate formaldehyde fixed, trypsin-treated rabbit erythrocyte;

with a pharmaceutically acceptable diluent or carrier.

The present invention discloses the function of immobilized galectin-8 as a matrix protein promoting cell adhesion. This invention is based in part on the adhesion of different cell types to bacterial plates coated with galectin-8 as exemplified herein. Whereas bacterial plates fail to support cell adhesion under serum-free conditions, galectin-8 immobilized on the plates promotes cell adhesion in a dose dependent manner, for all examined cell types. The adhesive function of galectin-8 involves protein-sugar interactions, as the adhesion to immobilized glutathione S-transferase (GST)-galectin-8 decreases upon addition of either thiodigalactoside (TDG) or galectin-8 specific polyclonal antibodies, while TDG alone does not affect cell adhesion as exemplified herein below.

The present invention further discloses that immobilized monoclonal mouse antibodies to galectin-8, like certain integrin antibodies, have the ability to promote cell adhesion in a dose dependent manner. The effects of the galectin-8 antibodies are specific and can not be mimicked by antibodies towards other cell surface proteins as exemplified herein below.

The present invention further discloses the signaling cascade induced upon cell adhesion to galectin-8 in vitro, exemplified by, but not limited to, the comparison of the tyrosine phosphorylation profile of cytoskeletal proteins in cells adherent to galectin-8 or fibronectin. Parental Chinese hamster ovary (CHO-P) cells adherent to galectin-8 show a diffused staining of Phospho-Tyr, which is not confined to focal adhesion sites. Tyrosine phosphorylation of the cytoskeletal proteins focal adhesion kinase (FAK) and paxillin in CHO-P and HeLa cells is induced by adhesion to galectin-8, albeit to a somewhat lesser extent compared to fibronectin.

In another aspect, the present invention discloses methods for inhibiting cell adhesion mediated by immobilized galectin-8 coating an adequate substrate or bound to the cell surface.

In one embodiment the inhibition of cell adhesion mediated by immobilized galectin-8 may be achieved by compositions comprising soluble galectin-8 or galectin-8 like proteins or fragment thereof selected from:

a. the protein galectin-8 having the amino acid sequence shown in FIG. 1 (SEQ ID NO:2) or its human homolog shown in FIG. 2 (SEQ ID NO:4);
  b. a protein having greater than 80 percent homology to all or part of amino acid sequence of SEQ. ID NO:2 or SEQ ID NO:4;
  c. a protein of (a) or (b) in which one or more amino acid residues have been added, deleted, replaced or chemically modified without substantially affecting the biological activity of the protein;
  d. a biological active fragment of any one of (a–c);
  e. an homologous polypeptide to that of any one of (a–d) derived from another mammal which has a similar biological activity of that of (a) or (b) or (c) or (d);

further comprising a pharmaceutically acceptable diluent or carrier.

The inhibitory effect of soluble galectin-8 is not restricted to one cell type, and it effectively inhibits, albeit with a different potency, the adhesion of many cell types. As exemplified herein, pre-incubation of soluble galectin-8 with HeLa cells markedly inhibits the subsequent cell adhesion to fibronectin-coated plates (after removal of unbound galectin). Therefore, soluble galectin-8 can negatively regulate cell-matrix interactions by generation of anti adhesive complexes upon binding to cell surface receptors.

Inhibition of cell adhesion mediated by immobilized galectin-8 achieved by the compositions of the present invention is specific and therefore advantages to that achieved by compositions comprising other substances, exemplified by non-specific agents including serum proteins, anti-β1 integrin antibodies and EDTA.

In yet another aspect, the present invention provides compositions for the specific inhibition of the expression of galectin-8 and galectin-8 like protein, comprising an antisense oligonucleotide. Full-length anti sense polyonucleotides for human galectin-8 has been previously disclosed by U.S. Pat. No. 5,869,289 and by Hadari et al, 2000 (*J Cell Sci* 113:2385–2397); however, as exemplified herein below, full-length anti-sense oligonucleotide for galectin-8 fail to influence the expression of galectin-8.

Thus, the present invention specifically relates to compositions comprising an oligonucleotide complementary to the nucleic acid sequence encoding galectin-8 and galectin-8 like proteins, selected from the group consisting of:

a. The nucleotide sequence of FIG. 1 (SEQ ID NO:1) or the human homolog of SEQ ID NO:3 (FIG. 2);
  b. an oligonucleotide having the nucleic acid sequence of a in which one or more codons has been added, replaced or deleted in a manner that the sequence essentially retains the same biological properties as the unaltered sequence;
  c. an oligonucleotide having nucleotide sequence, which is homologous to the DNA sequence of (a) or (b) having a similar biological activity to that of the sequence of (a) or (b);
  d. a fragment of the nucleotide sequence any one of (a–c) which essentially retains the biological activity of the unfragmented molecule; and
  e. an oligonucleotide molecule comprising the sequence of a fragment of any one of (a–d) and additional nucleotide sequences in the 3' and 5' ends; and
  f. an oligonucleotide according to any one of (a–e) containing modified backbones or non-natural intenucleoside linkages.

further comprising a pharmaceutical acceptable diluent or carrier.

Currently preferred embodiments comprise a composition comprising oligonucleotide of 5 to 50 nucleotides in length, more preferably 10–40 nucleotides in length, most preferably 15–30 nucleotides in length.

One currently most preferred embodiment comprises antisense oligonucleotides hybridizing to the sequences encoding the "hinge region" of galectin-8. These most preferred embodiments will be complementary to all or part of the coding sequence for amino acids 152–182 of hGalectin-8 (designated herein as SEQ ID NO:5), namely:

```
TTT AGC TTC AGC TCG GAC TTA CAA AGT ACC CAA GCA
TCT AGT CTG GAA CTG ACA GAG ATA AGT AGA GAA AAT
GTT CCA AAG TCT GGC ACG
```

Clearly it is possible to use other oligonucleotide sequences, from other parts of the molecule, if they prove to specifically inhibit the expression of galectin-8. Nucleotide constructs comprising the antisense oligonucleotide sequences of the invention, and vectors comprising these constructs are also explicitly encompassed within the scope of the invention.

In yet another aspect, the present invention discloses a method for treating pathological disorders relating to abnormal cell growth. In one embodiment, the present invention discloses a method for treating pathological disorders wherein the over-proliferating cells are cancer cells. In more preferred embodiment, the present invention discloses a method for treating cancer cells over-expressing galectin-8 and galectin-8 like proteins.

In yet another preferred embodiment, the present invention discloses a method for treating cancer cells selected from, but not restricted to, the group consisting of breast, lung and prostate cancer.

In one currently most preferred embodiment, the present invention discloses a method for treating prostate cancer cells.

In a further embodiment, the present invention discloses a method for treating a pathological disorder related to abnormal cell growth comprising the step of administering to a subject in need thereof a therapeutically effective amount of a composition which is capable of specifically inhibiting cell adhesion mediated by immobilized (cell surface bound) galectin-8 and galectin-8 like protein.

In one embodiment, the composition capable of inhibiting cell adhesion mediated by immobilized galectin-8 and galectin-8 like protein comprises soluble galectin-8.

In yet further embodiments, the present invention discloses a method for treating a pathological disorder relating to abnormal cell growth comprising the step of administering to a subject in need thereof a therapeutically effective amount of a composition which is capable of modulating the amount of galectin-8 or galectin-8 like proteins of abnormal cells.

In one embodiment, the composition capable of modulating the amount of galectin-8 and galectin-8 like protein comprises anti-galectin-8 antibodies. Novel compositions comprise anti-galectin-8 antibodies specific to an epitope other than the hinge region.

In one embodiment, the composition capable of modulating the amount of galectin-8 and galectin-8 like protein is specifically capable of inhibiting the expression of galectin-8 and galectin-8 like proteins.

In one more preferred embodiment, the composition capable of inhibiting the expression of galectin-8 and galectin-8 like proteins comprises an antisense oligonucleotide complementary to the nucleic acid sequence encoding galectin-8 and galectin-8 like proteins and fragments thereof.

The present invention provides antisense compounds, particularly oligonucleotides, for use in modulating the function of nucleic acid molecules encoding galectin-8, ultimately modulating the amount of galectin-8 produced. This is accomplished by providing oligonucleotides that specifically hybridize with nucleic acids encoding galectin-8, preferably hybridizing with mRNA transcripts encoding galectin-8, most preferably oligonucleotides specifically hybridizing to the coding sequence for amino acids 152–182 of human galectin-8 (SEQ ID NO:5).

The relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the targets are nucleic acids encoding galectin-8; in other words, a gene encoding galectin-8, or mRNA expressed from the galectin-8 gene. mRNA which encodes galectin-8 is presently the preferred target. The targeting process also includes determination of a site or sites within the nucleic acid sequence for the antisense interaction to occur such that modulation of gene expression will result.

Use of antisense oligonucleotides is well known in the art. For example U.S. Pat. No. 6,228,642 describes methodology and terminology related to antisense technology. The teachings of this patent are incorporated herein in their entirety by reference. The following text includes non-limitative examples for such methods and terminology.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes).

It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding galectin-8, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region.

The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a pre-mRNA transcript to yield one or more mature mRNAs. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of galectin-8. In the context of this invention "modulation" means inhibition or stimulation; i.e., either a decrease or increase in expression. This modulation can be measured in ways which are routine in the art, for example by Northern blot assay of mRNA expression, or reverse transcriptase PCR, or by Western blot or ELISA assay of protein expression, or by an immunoprecipitation assay of protein expression. In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States Patents that teach the preparation of the above phosphorus-containing linkages include, but are not limited to U.S. Pat. Nos. 4,469,863; 5,278,302; 5,587,361; and references therein.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,618,704; 5,677,439; and references therein.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States Patents that teach the preparation of PNA compounds include, but are not limited to, U.S. Pat. Nos.: 5,539,082; 5,714,331; and 5,719,262. Further teaching of PNA compounds can be found in Nielsen et al 1991 (*Science* 254:1497–1500).

Other preferred embodiments of the invention are oligonucleotides with phosphorothioate backbones and oligonucleosides with heteroatom backbones, and in particular —CH$_2$—NH—O—CH$_2$—, —CH$_2$—N(CH$_3$)—O—CH$_2$— [known as a methylene (methylimino) or MMI backbone], —CH$_2$O—N(CH$_3$)CH$_2$—, —CH$_2$—N(CH$_3$)—N(CH$_3$)—CH$_2$— and —O—N(CH$_3$)—CH$_2$—CH$_2$— [wherein the native phosphodiester backbone is represented as —O—P—O—CH$_2$—] of U.S. Pat. No. 5,489,677, and the amide backbones of U.S. Pat. No. 5,602,240. Also preferred are oligonucleotides having morpholino backbone structures of U.S. Pat. No. 5,034,506.

Modified oligonucleotides may also contain one or more substituted sugar moieties. Preferred oligonucleotides comprise one of the following at the 2' position: OH; F; O—, S—, or N-alkyl, O-alkyl-O-alkyl, O—, S—, or N-alkenyl, or O—, S—or N-alkynyl, wherein the alkyl, alkenyl and alkynyl may be substituted or unsubstituted C1 to C10 alkyl or C2 to C10 alkenyl and alkynyl. Particularly preferred are O[(CH$_2$)$_n$O]$_m$CH$_3$, O(CH$_2$)$_n$OCH$_3$, O(CH$_2$)$_2$ON(CH$_3$)$_2$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred oligonucleotides comprise one of the following at the 2' position: C1 to C10 lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al 1995 *Helv Chim Acta* 78:486–504) i.e., an alkoxyalkoxy group.

Other preferred modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'–5' linked oligonucleotides and the 5' position of 5'terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 5,597,909; 5,627,053; 5,670,633; and references therein.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering* 1990, pp. 858–859, Kroschwitz, J I ed. John Wiley & Sons, those disclosed by Englisch et al 1991 (*Angewandte Chemie, International Edition* 30:613–722), and those disclosed by Sanghvi Y S et al eds 1993 *Antisense Research and Applications*, CRC Press, Boca Raton, pp. 289–302. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-Methylcytosine substitutions have been shown to increase nucleic acid duplex stability by 0.6–1.2.degree. C. (Sanghvi Y S et al *Antisense Research and Applications*, CRC Press, Boca Raton, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 5,596,091; 5,614,617; 5,681,941; and references therein.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety cholic acid, a thioether, e.g., hexyl-S-tritylthiol a thiocholesterol, an aliphatic chain, e.g., dodecandiol or undecyl residues, a phospholipid, e.g., di-hexadecyl-rac-glycerol or trimethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

Representative United States patents that teach the preparation of such oligonucleotide conjugates include, but are not limited to, U.S. Pat. Nos. 5,525,465; 4,667,025; 4,762,779; 5,688,941; and references therein.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids. Ribozymes are not comprehended by the present invention.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., fluoro- or 2'-O-methoxyethyl-substituted). Chimeric oligonucleotides are not limited to those with modifications on the sugar, but may also include oligonucleosides or oligonucleotides with modified backbones, e.g., with regions of phosphorothioate (P.dbd.S) and phosphodiester (P.dbd.O) backbone linkages or with regions of MMI and P.dbd.S backbone linkages. Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'-O—$CH_2CH_2OCH_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—$CH_2CH_2OCH_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred.

The oligonucleotides used in accordance with this invention may be conveniently and routinely made through the well-known technique of solid phase synthesis. Any other means for such synthesis may also be employed; the actual synthesis of the oligonucleotides is well within the talents of the routine experimenter. It is well known to use similar techniques to prepare oligonucleotides such as the phosphorothioates and 2'-alkoxy or 2'-alkoxyalkoxy derivatives, including 2'-O-methoxyethyl oligonucleotides (Martin P 1995 Helv Chim Acta 78:486–504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention. "Pharmaceutically acceptable salts" are physiologically and pharmaceutically acceptable salts of the nucleic acids of the invention: i.e., salts that retain the desired biological activity of the parent compound and do not impart undesired toxicological effects thereto (see, for example, Berge et al 1977 J of Pharma Sci 66:1–19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants. One or more penetration enhancers from one or more of these broad categories may be included.

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition.

Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.).

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the compositions of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al 1995 *Current Op Biotech* 6:698–708).

The pharmaceutical compositions of the present invention may be administered in a number of ways depending upon whether local or systemic treatment is desired and upon the area to be treated. Administration may be topical (including ophthalmic, vaginal, rectal, intranasal, epidermal, and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents such as those used for tumor and cancer treatment. When used with the compounds of the invention, such chemotherapeutic agents may be used individually, sequentially, or in combination with one or more other such chemotherapeutic agents.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on the $EC_{50}$ found to be effective during in vitro and in vivo animal models. In general, dosage is from 0.01 μg to 100 mg per kg of body weight, and may be given once or more daily, or at longer intervals. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 mg per kg of body weight, once or more daily, or at longer intervals if appropriate.

Thus, in the context of this invention, by "therapeutically effective amount" is meant the amount of the compound that is required to have a therapeutic effect on the treated individual. This amount, which will be apparent to the skilled artisan, will depend upon the age and weight of the individual, the type of disease to be treated, perhaps even the gender of the individual, and other factors which are routinely taken into consideration when designing a drug treatment. A therapeutic effect is assessed in the individual by measuring the effect of the compound on the disease state. Inhibition is presently a preferred form of modulation.

The principles of the invention, for using galectin-8 and galectin-8 like proteins as modulators of cell adhesion, as well as the use of antibodies or antisense molecules for the treatment of tumors, may be better understood with reference to the following non-limiting examples.

EXAMPLES

Experimental Procedures

Materials Bacterially expressed recombinant galectin-8 (galectin-8) and GST-galectin-8 were generated as previously described (Hadari et al, 1995 *J Biol Chem* 270:

3447–3453). Restriction enzymes were purchased from New England BioLabs, Inc. (Beverly, Mass.). Echistatin, TRITC-labeled phalloidine, Crystal Violet, fibronecting, and glutathione-agarose beads were purchased from Sigma Chemicals Co. (St. Louis, Mo.).

Antibodies Affinity-purified polyclonal antibodies (1.1) against galectin-8 were generated as described (Hadari et al, supra). Monoclonal antibodies (106.1) against recombinant galectin-8 were generated by established procedures (Eshhar, Z 1985 in *Hybridoma in Biotechnology and Medicine* Springer T ed, pp. 1–41, Plenum Press) and were purified over protein-G coupled to Sepharose. Peroxidase-conjugated affinity purified goat anti-mouse IgG (H+L), Cy3-conjugated, and FITC-conjugated affinity purified $F(ab')_2$ fragment of goat anti-mouse IgG (H+L) were purchased from Jackson Immunoresearch Laboratories, Inc. Monoclonal anti-vinculin (hVin-1), and monoclonal anti-P-Tyr (PT-66), were purchased from Sigma Chemicals Co. (St. Louis, Mo.). Anti-paxillin, and anti-FAK monoclonal antibodies were obtained from Transduction Labs (Lexington, Ky.). Monoclonal anti-fibronectin antibodies were generated by B. Geiger (Weizmann institute, Rehovot, Israel). Affinity-purified polyclonal antibodies directed towards the insulin receptor α subunits were purchased from Santa Cruz Biotechnology (Santa Cruz, Calif.). Monoclonal antibodies (IgG fraction), directed towards the extracellular domain of ErbB-2 (Klapper L N et al 1997 *Oncogene* 14:2099–2109) were a generous gift of Y. Yarden (Weizmann institute, Rehovot, Israel).

Cell cultures Human non-small cell lung carcinoma H1299 cells and rat hepatoma (Fao) cells were grown in RPMI medium containing 10% fetal calf serum (FCS). Chinese Hamster Ovary (CHO-P) cells and CHO-T cells {transfected with human insulin receptor (Paz K et al 1999 *J Bio. Chem* 274:28816–28822)} were grown in F12 medium containing 10% FCS. HeLa cells were grown in MEM medium containing 10% FCS. Human keratinocytes (HaCaT cells), human hepatoma Hep-G2 and NIH-hIR mouse fibroblasts {over expressing the insulin receptor (Jui H Y et 1996 *Biochemistry* 35:14326–14330)} were grown in DMEM medium containing 10% FCS. N87 human gastric tumor cells were grown in DMEM medium containing 10% FCS supplemented with 1 mM sodium pyruvate.

Cell adhesion assay Bacterial or tissue culture plates were precoated for 2 h at 22° C. with the indicated ligands (in PBS) or antibodies. Cells, grown on tissue culture plates, were detached from the plates with 5 mM EDTA, washed with PBS, resuspended in serum-free medium, and re-seeded on the coated plates. At the indicated times cells were washed, and the adherent cells were counted. Alternatively, adherent cells were stained with 0.2% crystal violet in PBS containing 20% methanol for 30 min at 22° C. Excess dye was removed by three washes with water, and cells were solubilized in 1% SDS for 1 h at 22° C. Cell binding was quantified by measuring the absorbance at 540 nm in an ELISA plate reader-TECAN (Spectra, Austria). Specific binding was defined as the difference between the absorbance of cells binding to ligand-coated wells and the absorbance of cells binding to BSA-coated wells. All assays were performed in triplicate.

Binding of serum proteins to GST-galectin-8 GST-galectin-8 or GST (0.5 mg each) were immobilized on 200 µl Glutathione-Agarose beads. Following 2 h incubation at 4° C., the beads were washed and further incubated for 2 h at 4° C. with 5 ml of 100% fetal calf serum. The beads were intensively washed 3 times with 1% Triton X-100 in PBS, and the bound proteins were eluted by 2 h incubation at 4° C. with 100 µl of either lactose, glucose or NaCl (150 mM each). The eluted proteins were suspended in Laemmli's Sample buffer, and resolved by 10% SDS-PAGE.

Preparation of cell extracts Cell extracts were prepared in Buffer A (25 mM Tris/HCl, 25 mM NaCl, 0.5 mM EGTA, 2 mM sodium orthovanadate, 10 mM NaF, 10 mM sodium pyrophosphate, 80 mM β-glycerophosphate, 1% Triton X-100, 0.5% deoxycholate, 0.5% SDS, 5 µg/ml leupeptin, 10 µg/ml trypsin inhibitor and 1 mM PMSF, pH 7.5). Insoluble material was removed by 15 min centrifugation (12,000×g) at 40° C. Supernatants were mixed with 5× concentrated Laemmli's sample buffer (34), boiled for 5 min, and resolved on 10% SDS-PAGE under reducing conditions, transferred to nitrocellulose membrane (Schleicher and Schuell GmbH, Dassel, Germany), and Western immunoblotted with the indicated antibodies.

Immunoprecipitation—Cell extracts (1–2 mg protein) were incubated for 16 h at 4° C. with monoclonal focal adhesion kinase (FAK) or paxillin antibodies, followed by additional incubation for 2 h at 4° C. with 30 µl protein G-Agarose beads. Immunocomplexes were washed twice with buffer B (25 mM Tris/HCl, 25 mM NaCl, 0.5 mM EGTA, 2 mM sodium orthovanadate, 10 mM NaF, 10 mM sodium pyrophosphate, 80 mM β-glycerophosphate, 1% Triton X-100, 5 µg/ml leupeptin, 10 µg/ml soybean trypsin inhibitor and 1 mM PMSF, pH 7.5), and once with PBS. Samples were mixed with Laemmli's sample buffer, boiled for 5 min, resolved by means of 10% SDS-PAGE, and were immunoblotted with the indicated antibodies.

Example 1

Immobilized Galectin-8 Functions as an Extracellular Matrix Protein and Supports Cell Adhesion.

Figure 4:
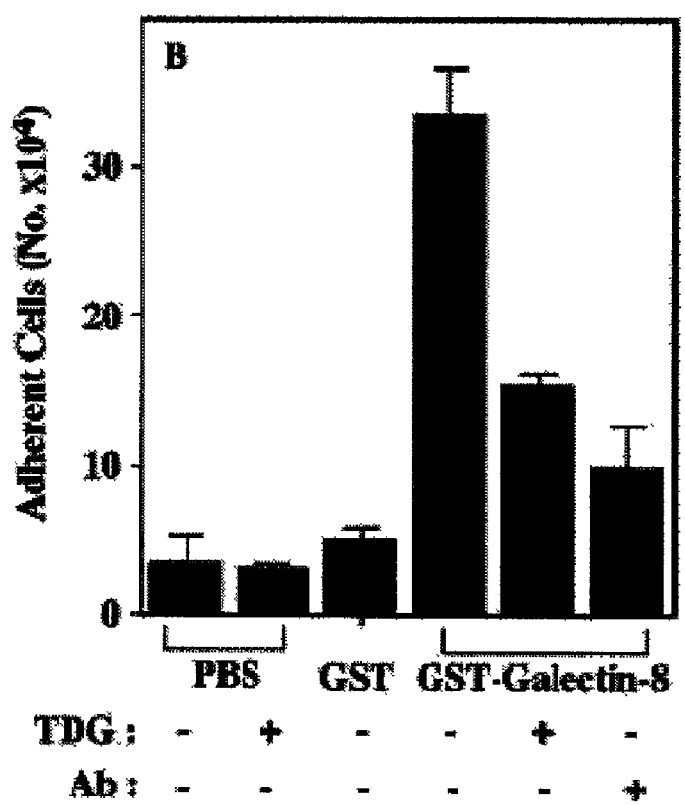
FIG. 4 Specificity of cell adhesion to galectin-8

Adhesion of HeLa cells to bacterial plates coated with galectin-8 was studied. 96-well bacterial plates were pre-coated with various concentrations of galectin-8 or fibronectin. HeLa, CHO-T NIH-hIR or Fao cells were detached from culture plates with 5 mM EDTA, washed with phosphate buffered saline (PBS) and seeded in serum-free medium on the coated wells. Following 2 h of incubation at 37° C., cells were washed and stained with crystal violet, and the number of the adherent cells was determined. While bacterial plates fail to support cell adhesion under serum-free conditions, galectin-8 immobilized on the plates promoted cell adhesion in a dose-dependent manner (FIG. 3A). Higher doses of added galectin-8 than fibronectin were required to support cell adhesion. Still, when applied to the plates at a maximal dose, galectin-8 (2.5 µM) was as effective as fibronectin (0.1 µM). Similar results were obtained when adhesion of CHO-T, NIH-hIR, or Fao cells was studied (FIGS. 3, B–D). These findings indicate that galectin-8 could function as an ECM protein for different cell types. The adhesion to immobilized GST-galectin-8 was abolished upon addition of either thiodigalactoside (TDG), or galectin-8 specific polyclonal antibodies (FIG. 4). TDG alone did not affect cell adhesion (not shown). These findings suggest that the adhesive functions of galectin-8, like its anti-adhesive effects, involve protein-sugar interactions.

Example 2

Promotion of Cell Adhesion by Monoclonal Anti-Galectin-8 Antibodies

Certain integrin antibodies are characterized by their unique ability to promote cell adhesion (Neugebauer K M &

Figure 5:
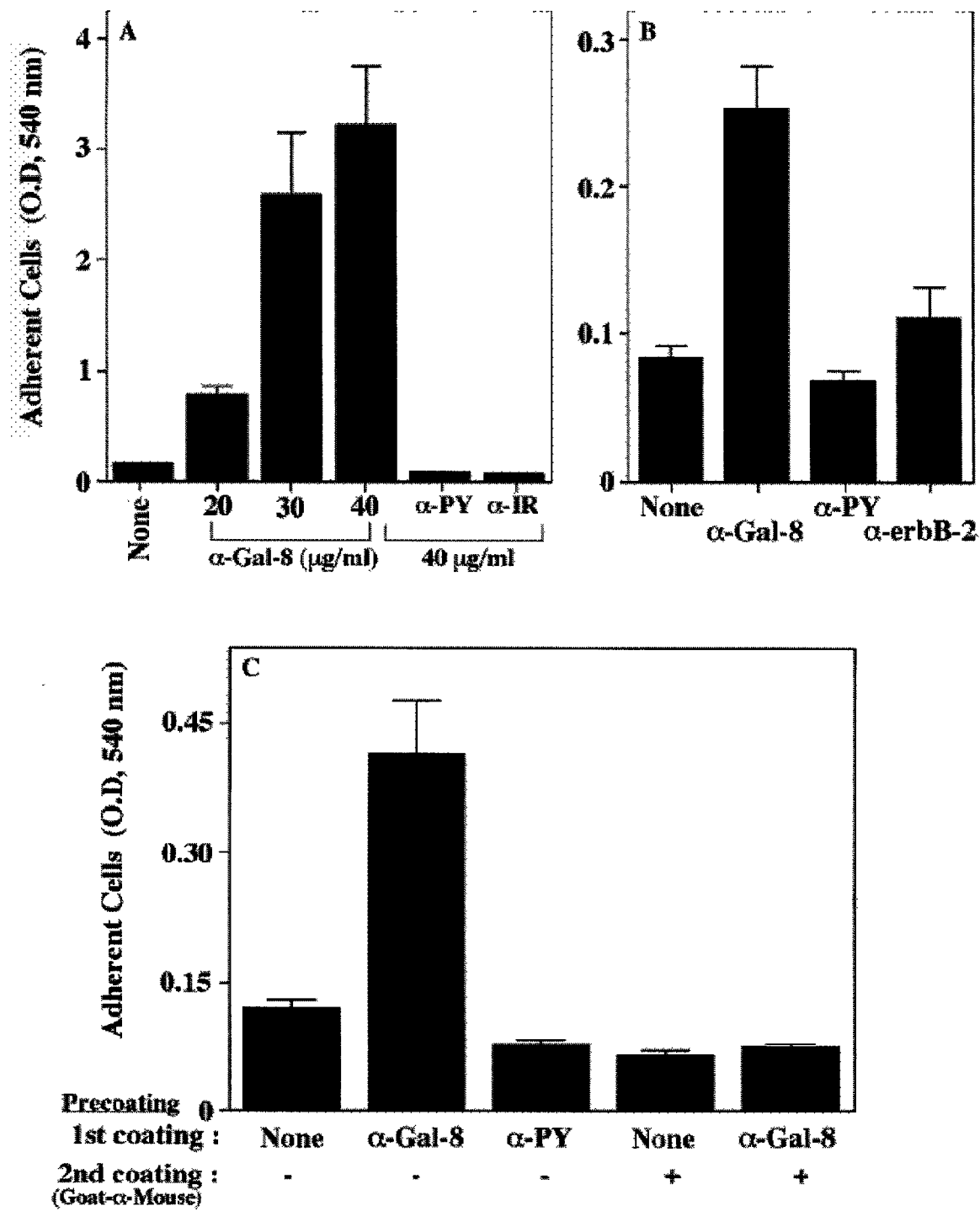
FIG. 5 Adhesion of Fao (A), N87 (B), or HeLa (C) cells to immobilized anti-galectin-8 monoclonal antibodies compared to their adhesion to anti-phospho-tyrosine antibodies ($\alpha$-PY) or anti-insulin receptor (extracellular) $\alpha$ subunit ($\alpha$-IR).

Reichardt L F 1991 *Nature* 350:68–71). Since galectin-8 forms cell-surface complexes with integrins, the effects of galectin-8 antibodies on cell adhesion were studied. The adhesion conditions (bacterial plates, serum free medium) were selected such that basal adhesion was negligible. 96-well bacterial plates were precoated (2 h at 22° C.) with 100 µl of monoclonal antibodies (106.1), anti-phospho-Tyr (α-PY), anti-insulin receptor (extracellular) α subunit (α-IR), goat anti-mouse antibodies or anti-erb2 monoclonal antibodies, each at 40 µg/ml unless otherwise indicated. When indicated, plates coated with monoclonal antibodies (106.1) were further coated (2 h at 22° C.) with 50 µl of goat anti-mouse antibodies. $4 \times 10^5$ Fao (FIG. 5A), N87 (FIG. 5B) or HeLa (FIG. 3C) cells were detached from cultured plates with 5 mM EDTA, washed with PBS, and seeded at 37° C. in serum-free medium on the coated wells. Following 2 h of incubation at 37° C., cells were washed and stained with crystal violet, and the number of adherent cells was determined. Similar to integrin antibodies, immobilized monoclonal mouse antibodies to galectin-8 effectively promoted cell adhesion in a dose-dependent manner (FIG. 5A). The effects of the galectin-8 antibodies were specific and could not be mimicked by P-Tyr antibodies or antibodies towards other cell surface proteins such as the extracellular α subunit of the insulin receptor or the extracellular domain of Erb2 (FIG. 5B). Moreover, the adhesive effects of the antibodies were abolished upon addition of goat-anti mouse antibodies (FIG. 5C). These findings further establish the role of galectin-8 as a potential physiological modulator of cell adhesion.

Example 3

Characterization of Cell Adhesion by Immobilized Galectin-8

The cytoskeletal organization mediated by immobilized galectin-8 and its kinetics was examined by adhesion of different cell types to pre-coated glass plates. Cover glasses were precoated for 2 h at 22° C. with 1 ml of fibronectin (0.04 µM) or galectin-8 (0.7 µM). HeLa, NIH-hIR or CHO-P cells were grown on tissue culture plates and incubated for 16 h in serum-free medium. Cells were then detached from the culture plates with 5 mM EDTA, washed, incubated in suspension for 30 min at 37° C. and seeded on the precoated cover glasses in a serum free medium. After incubation for 2 h at 37° C. (FIG. 6), or the indicated time (FIG. 7), cells were washed, fixed and stained. Actin staining was performed by incubation with tetramethylrhodamine isothiocyanate-labeled phalloidin. Immunostaining of paxilin, vinculin or phospho-Tyr was performed as described under "Experimental Procedures".

Figure 6:
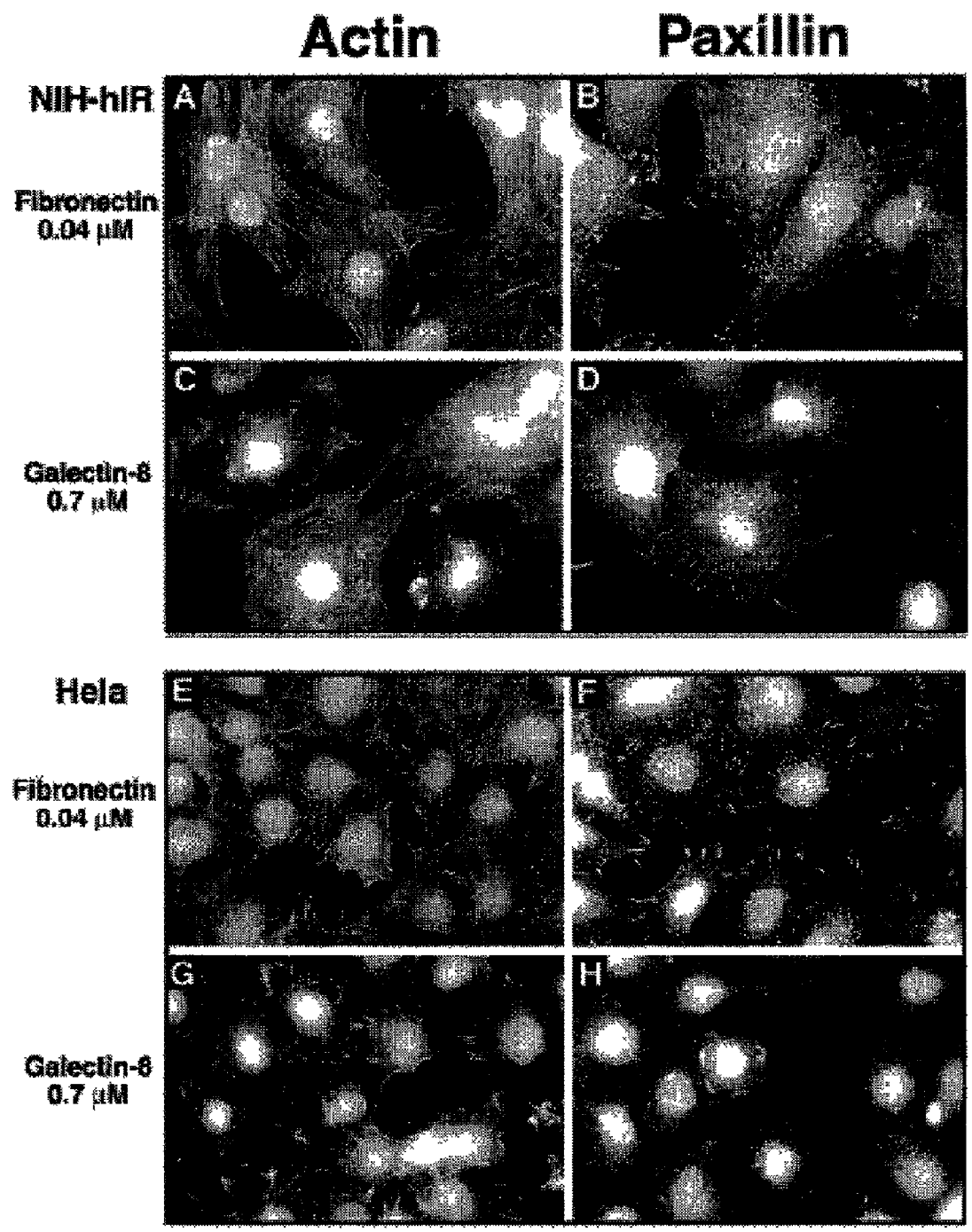
FIG. 6 Cytoskeletal organization of cells adherent to galectin-8 or fibronectin
Figure 7:
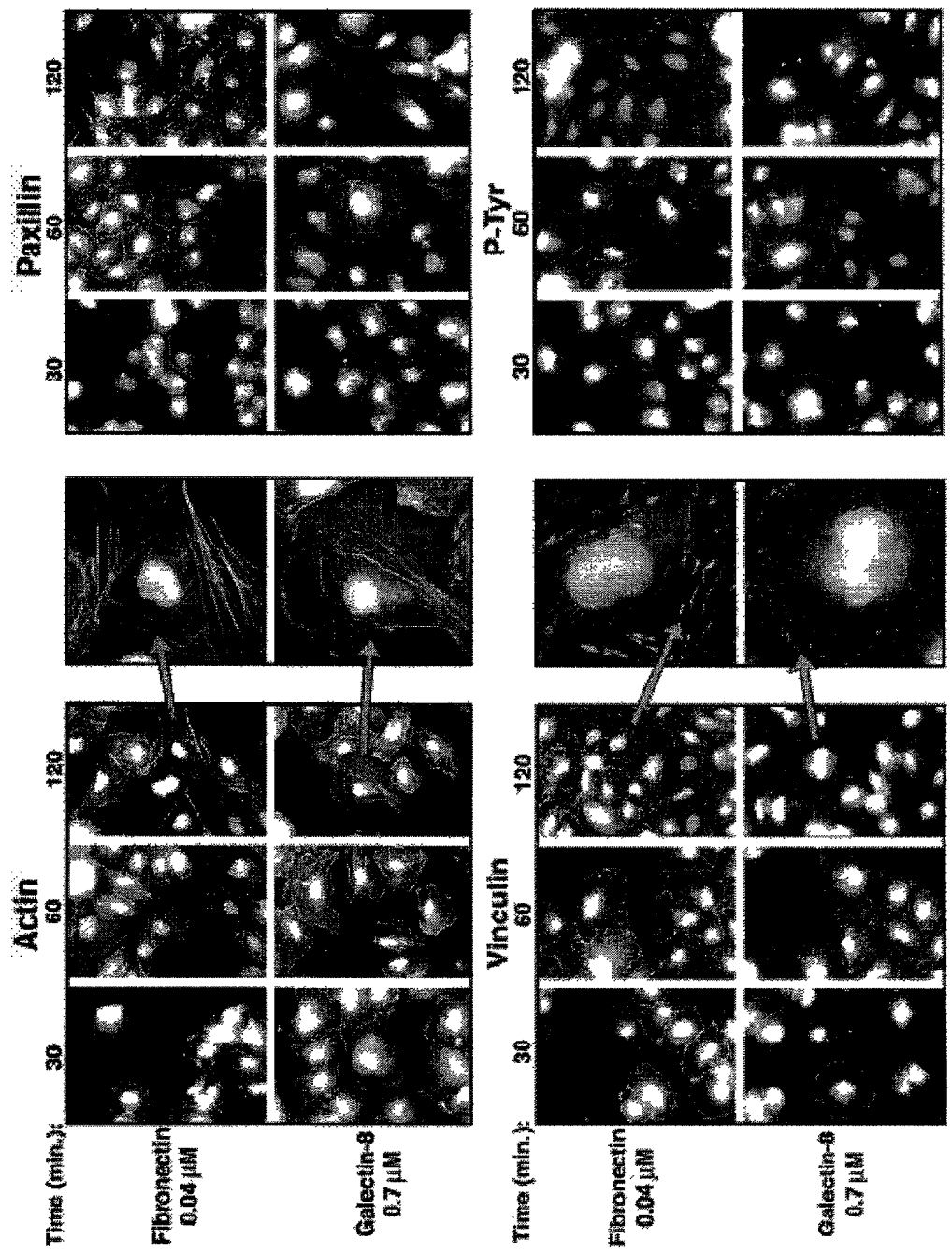
FIG. 7 Cytoskeletal organization in cells adherent to galectin-8 or fibronectin over time.

Immobilized galectin-8, like fibronectin, induced attachment and spreading of all cell types examined. However, marked differences were noted in the cytoskeletal organization of the cells attached to galectin-8 compared to fibronectin. The differences were not prominent following 30 min incubation (FIG. 7), but became more evident as the adhesion process progressed for 2 hours. Prominent stress fibers that traverse the cell body were readily observed in fibronectin adherent cells, but were less abundant in cells adherent to galectin-8 (FIG. 6, A vs. C and E vs. G; and enlargement of FIG. 7). Second, while vinculin and paxillin were associated with large focal contacts in cells adherent to fibronectin, the number and size of vinculin-and paxillin-containing focal contacts was reduced in cells attached to galectin-8. In fact, many adhesion sites, especially in HeLa cells, were devoid of paxillin altogether. Similarly, NIH-hIR, HeLa or CHO-P cells seeded on fibronectin formed many focal adhesions throughout their entire ventral surface, while vinculin- or paxillin-containing plaques were rather small in size and were primarily limited to the cell periphery in cells seeded on galectin-8 (FIGS. 6&7). In accordance with the observed differences in cytoskeletal organization, CHO-P cells adherent to galectin-8 showed a diffused staining of phospho-Tyr, which was not confined to focal adhesion sites (FIG. 7).

Example 4

Signaling Cascade Induced Upon Cell Adhesion to Galectin-8

Figure 8:
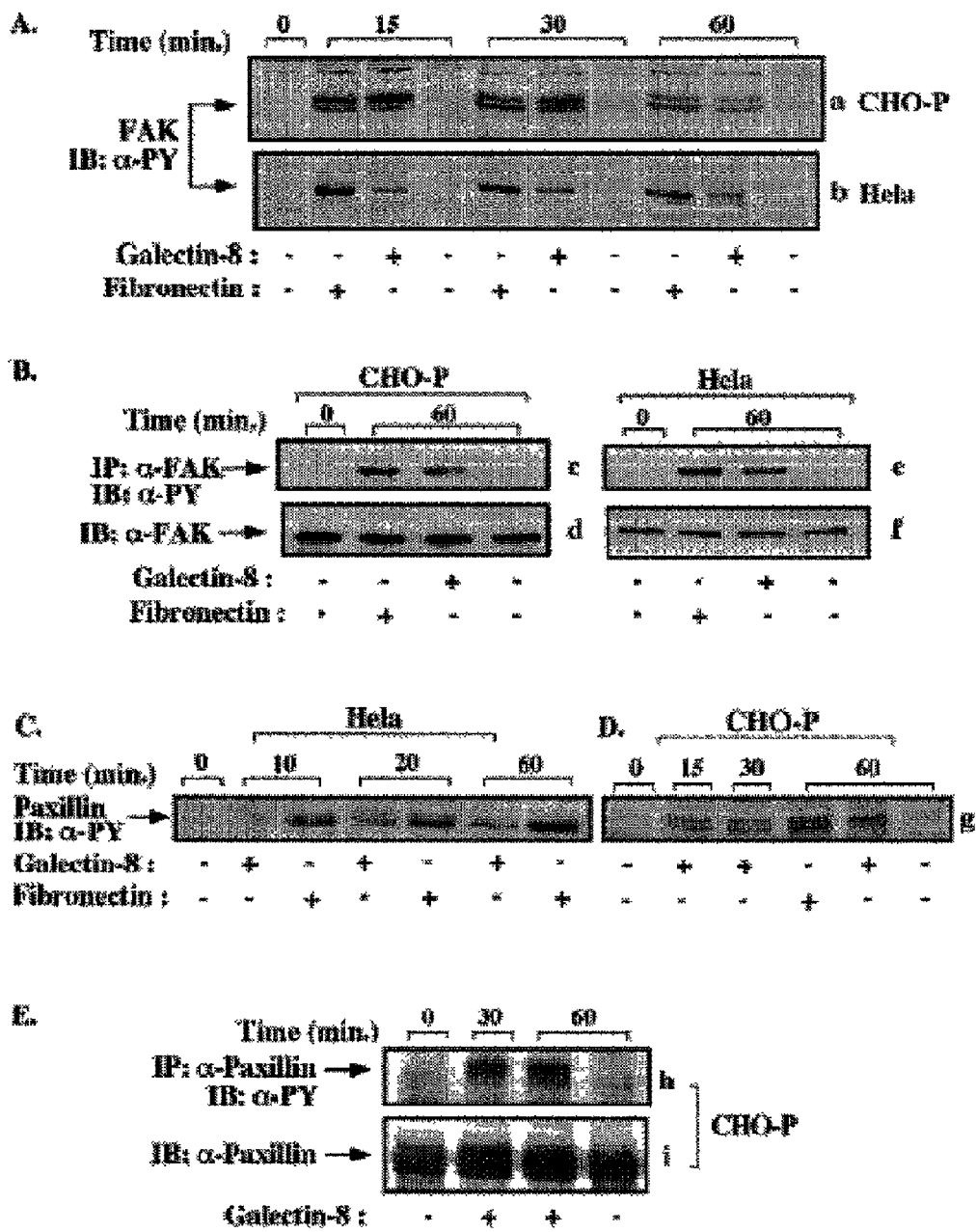
FIG. 8 Tyrosine phosphorylation of focal adhesion factor (FAK) and paxillin, induced upon cell adhesion to galectin-8 or fibronectin.

As a first step in elucidating the signaling cascade induced upon cell adhesion to galectin-8, the tyrosine phosphorylation profile of cytoskeletal proteins in cells adherent to galectin-8 or fibronectin was compared. Six cm bacterial plates were precoated with 5 ml of galectin-8 (0.7 µM) or fibronectin (0.04 µM) for 2 h at 22° C. HeLa or CHO-P cells, grown on tissue culture plates for 16 h in serum-free medium, were then detached from plates with 5mM EDTA (FIGS. 8A, B, D, E) or with 0.05% trypsin and 2 mM EDTA (FIG. 8C) washed, incubated in suspension for 30 min (A, B, D, E) or 60 min (E) at 37° C. in serum-free medium, and seeded in serum-free medium on the coated plates. Following incubation at 37° C. at the indicated times, cells were washed and extracted as described under "Experimental Procedures". Proteins (100 µg) were resolved by 10% SDS-PAGE, transferred to nitrocellulose membranes, and Western immunoblotted with anti phospho-Tyr antibodies (FIG. 8 panels a, b, g), Anti-FAK (FIG. 8*f*) or anti paxillin (FIG. 8*i*) antibodies. Alternatively, cell extracts were subjected to immunoprecipitation with anti-FAK (FIG. 8B) or anti-paxillin (FIG. 8E) antibodies, resolved by 10% SDS-PAGE, transferred to nitrocellulose membranes, and Western immunoblotted with anti-P-Tyr (FIG. 8 panels c, e, h) or anti FAK antibodies (FIG. 8*d*). Consistent with previous studies, Tyr phosphorylation of focal adhesion kinase (FAK) and paxillin were largely diminished upon detachment of the cells from culture plates (FIG. 8 time zero; and 60 min without galectin-8 or fibronectin). Re-adhesion of CHO-P or HeLa cells onto fibronectin-coated plates induced Tyr phosphorylation of FAK and paxillin that remained elevated for at least 60 min post-adhesion. Reduced levels of Tyr phosphorylation of FAK and paxillin were observed at all time points when HeLa cells adhered onto galectin-8-coated plates (FIGS. 8A and C). This reduction was less prominent when CHO-P cells adherent to galectin-8 were studied. The identity of pp125 and pp74 as FAK and paxillin, respectively, was confirmed by immunoprecipitation with FAK- or paxillin-specific antibodies (FIGS. 8B and D).

Example 5

Inhibition of Cell Adhesion by Soluble Galectin-8.

Figure 9:
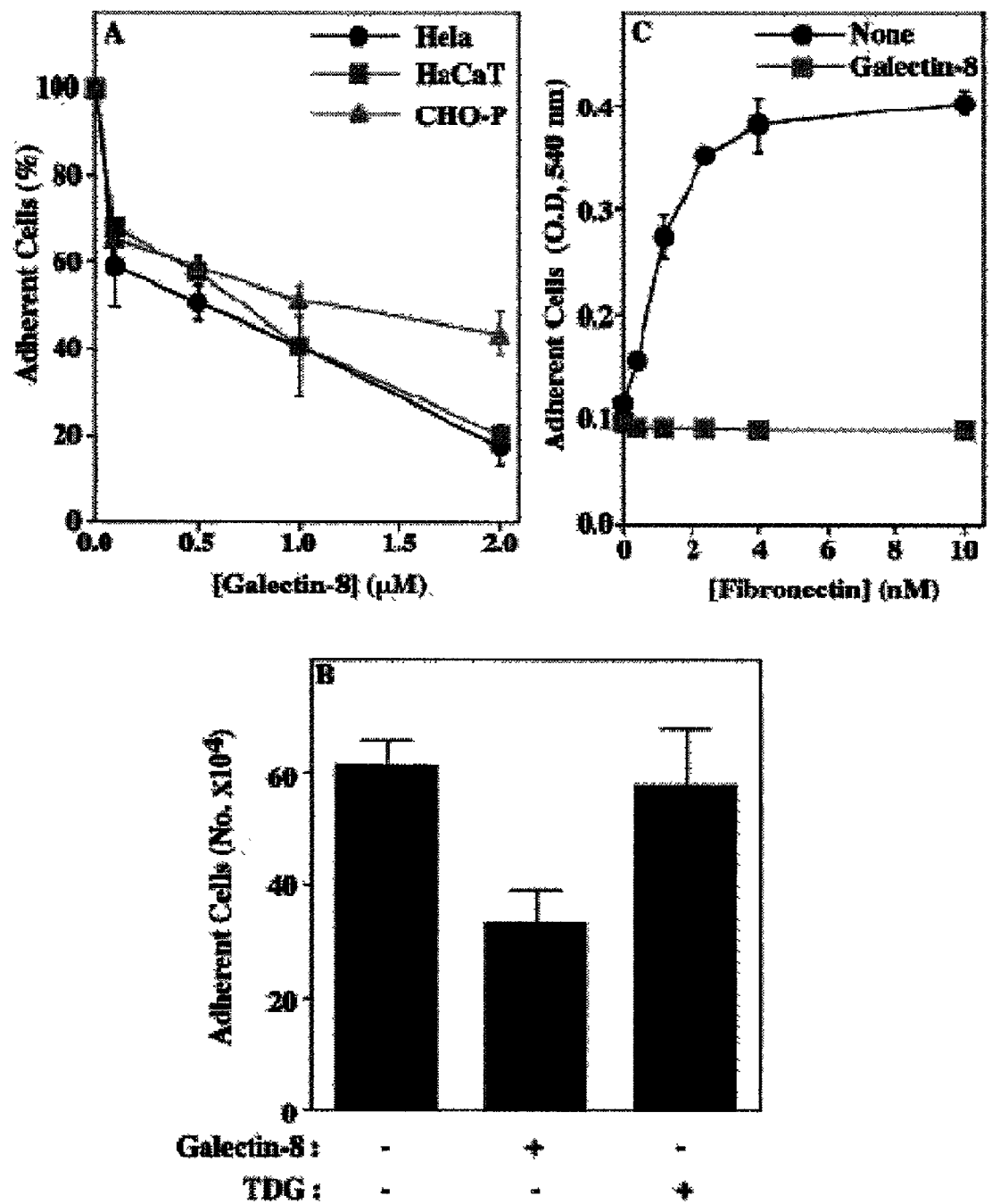
FIG. 9 Inhibition of cell adhesion mediated by soluble galectin-8: (A) Inhibition of HeLa, HaCaT and CHO cells adhesion in the presence of soluble galectin-8. (B) The effect of thiodigalactoside (TDG) on cell adhesion mediated by soluble galectin-8. (C) Comparison of the effect of soluble galectin-8 on adhesion of HeLa cells to galectin-8 or fibronectin.

HeLa, HaCaT, and CHO-P cells ($3 \times 10^5$) were detached from culture plates with 5 mM EDTA, washed with PBS, and resuspended in medium containing 10% FCS. Cells were seeded on 24-well Costar plates in the absence or in the presence the indicated concentrations of galectin-8. Following 2 h incubation at 37° C., cells were washed and the number of adherent cells was counted. Values are mean±SD of duplicate measurements of a representative experiment. As shown in FIG. 9A, soluble galectin-8 effectively inhibited (albeit with a different potency) the adhesion of all cell types examined. High doses (2 µM) of galectin-8 inhibited 50–80% the number of adherent HaCaT, HeLa, and CHO-P cells, as well as adhesion of Hep-G2 and PC-12 cells (not shown). To evaluate the protein-sugar interactions involved in the inhibitory effect of soluble-galectin-8 on cell adhesions HeLa cells ($3 \times 10^5$) were detached from culture plates with 5 mM EDTA, washed with PBS, and seeded on 24-well Costar plates in the absence (control) or in the presence of galectin-8 (1 µM), or galectin-8 and TDG (10 mM). Following 2 h incubation at 37° C., cells were washed and the number of adherent cells was counted. As shown in FIG. 9B, galectin-8 effects were abolished upon addition of thiodigalactoside (TDG), which blocks lectin-carbohydrate interactions. TDG alone (10 mM) did not affect cell adhesion (data not shown). Soluble galectin-8 also inhibited fibronectin-mediated cell adhesion: 96-well tissue culture plates were precoated with 0.1 ml of various fibronectin concentrations for 1 h at 37° C. and further blocked with 1% BSA for 1h at 37° C. HeLa cells ($1 \times 10^5$) were detached from culture plates with 5 mM EDTA, and washed with PBS. Cells were incubated in suspension for 1 hour at 37° C. in serum-free medium, in the absence or the presence of Galectin-8 (2.5 µM). At the end of incubation cells were washed before being seeded on the fibronectin-coated wells. Following 2 h incubation at 37° C. cells were washed, stained with crystal violet and the number of adherent cells was determined using ELISA-reader at 540 nm. FIG. 9C shows that incubation of HeLa cells with soluble galectin-8 markedly inhibited cell adhesion to fibronectin-coated plates.

Example 6

Regulation of Galectin-8 Expression

Figure 10:
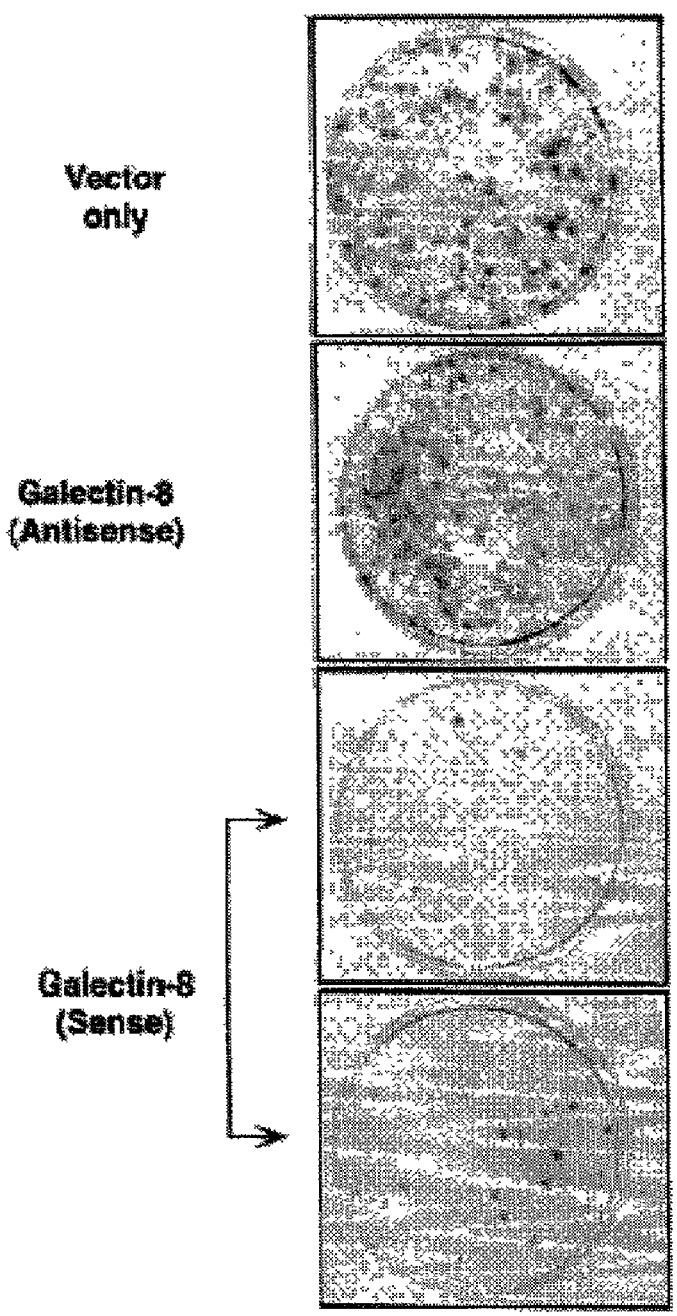
FIG. 10 Regulation of galectin-8 expression

Overexpression and antisense regulation of expression were tested in cell cultures as described previously (Hadari et al., 2000 J Cell Sci 113:2385–2397). $6 \times 10^9$ 1299 cells were transfected by electroporation (960 µF, 250 V) with 15 µg DNA of pcDNA-3 vector alone, or with a vector containing full-length rat galectin-8 cDNA in the sense or antisense orientation. Following transfection, cells were plated in non-selective medium (RPMI containing 10% Fetal Calf Serum (FTC), and 48 h thereafter, 0.8 mg/g of G-418 was added for selection of stable colonies. The medium (including G-418) was replaced every 3 days, and at day 21 colonies were stained by Crystal Violet (1.5 mg/ml in 10% ethanol and 12% formaldehyde). As shown in FIG. 10, over-expression of galectin-8 significantly reduced colony formation; however, full-length anti-sense failed to elicit any detectable effect on cell adhesion, as no difference was observed in colonies number when the cells were transfected with empty vector compared to vector containing the full-length antisense to galectin-8. Oligonucleotide antisense molecules may be optimized following this screening procedure, prior to in vivo testing.

Example 7

Treatment of Prostate Cancer with Soluble Galectin-8

Figure 11:
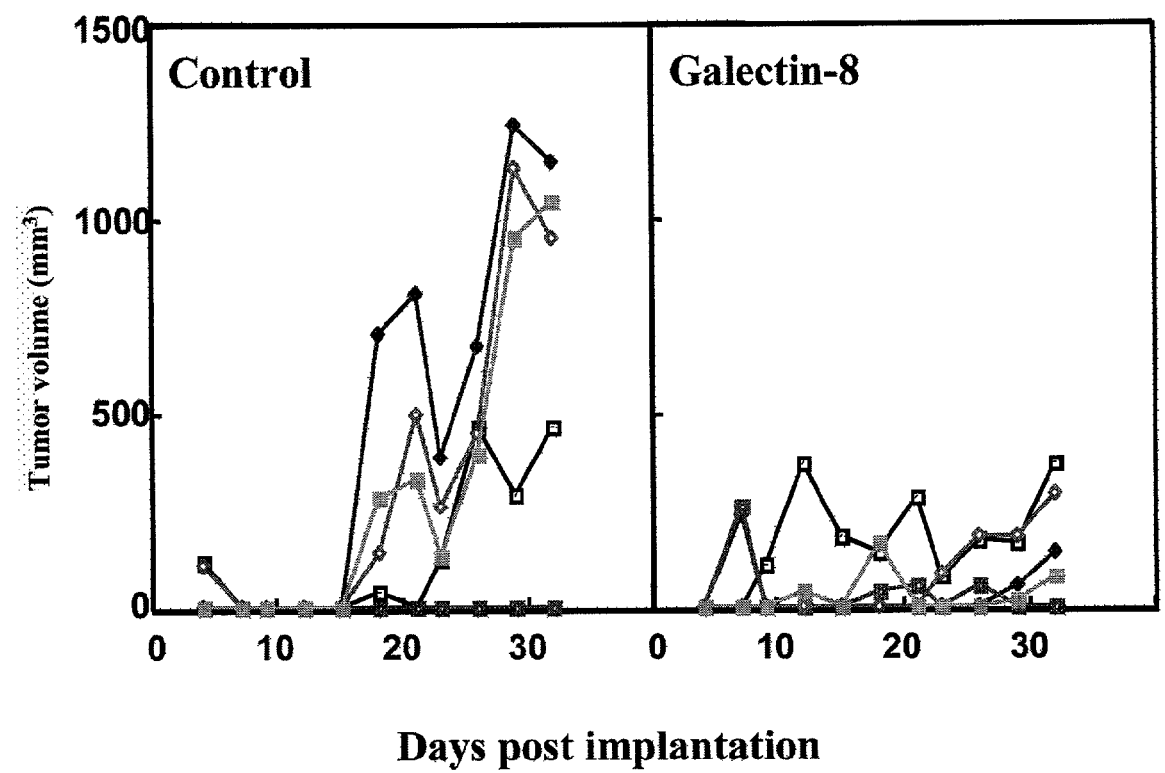
FIG. 11 Inhibition of growth of primary human prostate cancer xenografts in nude or NOD/SCID mice by soluble galectin-8

Prostate tumor explants, matched for weight and volume, were incubated (2 h at 37° C.) in the absence or presence of 70 µg/ml rGalectin-8, and were embedded in a synthetic ECM (Matrigel), prior to subcutaneous implantation into NOD/SCID mice. The formation of primary prostate tumors was evaluated by measuring the size of the growing tumors and by recording the serum levels of PSA. As shown in FIG. 11, explants incubated in the presence of galectin-8, showed a marked reduction in their growth rate. This was accompanied by a similar decrease in serum levels of PSA, compared to explants that were not treaded with the lectin. These findings implicate soluble rGalectin-8 as a strong inhibitor of prostate tumor growth in vivo.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention. Thus the expressions "means to . . . " and "means for . . . ", or any method step language, as may be found in the specification above and/or in the claims below, followed by a functional statement, are intended to define and cover whatever chemical structure, or whatever function, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

---

The invention claimed is:

1. A method for inhibiting cell adhesion mediated by cell-bound galectin-8, comprising exposing the cells to a pharmaceutical composition comprising as an active ingredient a soluble galectin-8 protein selected from the group consisting of SEQ ID NO:2 and SEQ ID NO:4.

2. A method for inhibiting adhesion of metastasized tumor cells in a subject, comprising administering to a subject in need thereof a therapeutically effective amount of a pharmaceutical composition comprising a soluble galectin-8 proteins selected from the group consisting of SEQ ID NO:2 and SEQ ID NO:4.

3. The method of claim 2, wherein the tumor cells over-express galectin-8.

4. The method of claim 2, wherein the tumor cells are selected from the group consisting of cancer cells of lung, liver, brain, bladder, prostate and melanoma.

5. The method of claim 4, wherein the tumor cells are prostate cancer cells.

* * * * *

SEQUENCE LISTING

```
<160> NUMBER OF SEQ ID NOS: 5

<210> SEQ ID NO 1
<211> LENGTH: 1247
<212> TYPE: DNA
<213> ORGANISM: Rattus norvegicus

<400> SEQUENCE: 1
aattcccccc ctggctgggg acaagttatt actttgagta atccttaaat gaagagtggg      60
taaagcccat atacggaaga gagactccag tcaacaatat caataagttg aagaagaaaa     120
```

-continued

```
atgttgtcct taagcaatct acaaaatatc atctataacc cgacaatccc ctatgtcagt    180
accattactg agcagttgaa gcctggctct ttgatcgtga tccgtggcca tgttcctaaa    240
gattcagaaa gattccaagt agactttcag catggcaaca gcctgaagcc gagagctgat    300
gtggccttcc actttaaccc tcgcttcaaa aggtccaact gcattgtttg taacacactg    360
acaaatgaga aatggggctg ggaggagatc acccacgaca tgccctttcag aaaagaaaag   420
tcctttgaga ttgtgatcat ggtgctaaag aacaaattcc acgtggctgt gaatggaaag    480
cacattctgc tgtatgccca caggatcaac ccagagaaga tagacacact gggcatcttc    540
ggcaaagtga acattcactc catcgggttc agattcagct cggatttaca gagtatggaa    600
acatctactc tgggactgac acagataagt aaagaaaata tacaaaagtc tggcaagctc    660
catttgagcc tgccatttga agcaaggttg aatgcctcca tgggccctgg acgaaccgtt    720
gtcgttaaag gagaagtgaa tacaaatgcc acaagcttta atgttgacct agtggcagga    780
aggtcaaggg atatcgctct gcacttgaac ccacgcctga atgtgaaagc gtttgtaaga    840
aactcctttc ttcaggatgc ctggggagaa gaggagagaa acattacctg cttcccattt    900
agttctggga tgtactttga gatgataatt tactgtgatg tccgagagtt caaggttgca    960
gtaaatggtg tgcacagcct ggagtacaag cacagattta agacctaag cagcatcgac    1020
acactagcag ttgatggcga tatccgtttg ctggatgtaa ggagctggta gctatcatga   1080
ctgccagaac cctggaaata caaatggct tatccgatac tggccatgtc aaatgcatct    1140
cgctttcacc acattgttat actgttaagt tgagctcgca caacatcaag tcctactggt   1200
gttgtcaggc ctggccatgc agtgtggcta cctctgaatt cccagga                 1247
```

<210> SEQ ID NO 2
<211> LENGTH: 316
<212> TYPE: PRT
<213> ORGANISM: Rattus norvegicus

<400> SEQUENCE: 2

```
Met Leu Ser Leu Ser Asn Leu Gln Asn Ile Ile Tyr Asn Pro Thr Ile
1               5                   10                  15

Pro Tyr Val Ser Thr Ile Thr Glu Gln Leu Lys Pro Gly Ser Leu Ile
            20                  25                  30

Val Ile Arg Gly His Val Pro Lys Asp Ser Glu Arg Phe Gln Val Asp
        35                  40                  45

Phe Gln His Gly Asn Ser Leu Lys Pro Arg Ala Asp Val His Phe His
    50                  55                  60

Phe Asn Pro Arg Phe Lys Arg Ser Asn Cys Ile Val Cys Asn Thr Leu
65                  70                  75                  80

Thr Asn Glu Lys Trp Gly Trp Glu Glu Ile Thr His Asp Met Pro Phe
                85                  90                  95

Arg Lys Glu Lys Ser Phe Glu Ile Val Ile Met Val Leu Lys Asn Lys
            100                 105                 110

Phe His Val Ala Val Asn Gly Lys His Ile Leu Leu Tyr Ala His Arg
        115                 120                 125

Ile Asn Pro Glu Lys Ile Asp Thr Leu Gly Ile Phe Gly Lys Val Asn
    130                 135                 140

Ile His Ser Ile Gly Phe Arg Phe Ser Ser Asp Leu Gln Ser Met Glu
145                 150                 155                 160

Thr Ser Thr Leu Gly Leu Thr Gln Ile Ser Lys Glu Asn Ile Gln Lys
                165                 170                 175
```

-continued

```
Ser Gly Lys Leu His Leu Ser Leu Pro Phe Glu Ala Arg Leu Asn Ala
            180                 185                 190

Ser Met Gly Pro Gly Arg Thr Val Val Lys Gly Glu Val Asn Thr
        195                 200                 205

Asn Ala Thr Ser Phe Asn Val Asp Leu Val Ala Gly Arg Ser Arg Asp
        210                 215                 220

Ile Ala Leu His Leu Asn Pro Arg Leu Asn Val Lys Ala Phe Val Arg
225                 230                 235                 240

Asn Ser Phe Leu Gln Asp Ala Trp Gly Glu Glu Arg Asn Ile Thr
            245                 250                 255

Cys Phe Pro Phe Ser Ser Gly Met Tyr Phe Gln Met Ile Ile Tyr Cys
            260                 265                 270

Asp Val Arg Glu Phe Lys Val Ala Val Asn Gly Val His Ser Leu Glu
        275                 280                 285

Tyr Lys His Arg Phe Lys Asp Leu Ser Ser Ile Asp Thr Leu Ala Val
        290                 295                 300

Asp Gly Asp Ile Arg Leu Leu Asp Val Arg Ser Trp
305                 310                 315
```

<210> SEQ ID NO 3
<211> LENGTH: 1106
<212> TYPE: DNA
<213> ORGANISM: Homo sapiens

<400> SEQUENCE: 3

```
cacagaagag actccaatcg acaagaagct ggaaaagaat gatgttgtcc ttaaacaacc      60
tacagaatat catctataac ccggtaatcc cgtttgttgg caccattcct gatcagctgg     120
atcctggaac tttgattgtg atacgtgggc atgttcctag tgacgcagac agattccagg     180
tagatctgca gaatggcagc agcatgaaac ctcgagccga tgtggccttt catttcaatc     240
ctcgtttcaa agggccggc tgcattgttt gcaatacttt gataaatgaa aaatggggac     300
gggaagagat cacctatgac acgcctttcc aaaagagaa aaagtctttt gagatcgtga     360
ttatggtgct gaaggccaaa ttccaggtgg ctgtaaatgg aaaacatact ctgctctatg     420
gccacaggat cggcccagag aaaatagaca ctctgggcat ttatggcaaa gtgaatattc     480
actcaattgg ttttagcttc agctcggact acaaagtac ccaagcatct agtctggaac     540
tgacagagat aagtagagaa atgttccaa gtctggcac gccccagctt aggctgccat     600
tcgctgcaag gttgaacacc cccatgggcc ctggacgaac tgtcgtcgtt aaaggagaag     660
tgaatgcaaa tgccaaaagc tttaatgttg acctactagc aggaaaatca aaggatattg     720
ctctacactt gaacccacgc ctgaatatta agcatttgt aagaaattct tttcttcagg     780
agtcctgggg agaagaagag agaaatatta cctctttccc atttagtcct gggatgtact     840
ttgagatgat aatttactgt gatgttagag aattcaaggt tgcagtaaat ggcgtacaca     900
gcctggagta caaacacaga tttaaagagc tcagcagtat tgacacgctg gaaattaatg     960
gagacatcca cttactggaa gtaaggagct ggtagcctac ctacacagct gctacaaaaa    1020
ccaaaataca gaatggcttc tgtgatactg gccttgctga aacgcatctc actgtcattc    1080
tattgtttat attgttaaaa tgacct                                         1106
```

<210> SEQ ID NO 4
<211> LENGTH: 318
<212> TYPE: PRT
<213> ORGANISM: Homo sapiens -continued

<400> SEQUENCE: 4

```
Met Met Leu Ser Leu Asn Asn Leu Gln Asn Ile Ile Tyr Asn Pro Val
1               5                   10                  15

Ile Pro Phe Val Gly Thr Ile Pro Asp Gln Leu Asp Pro Gly Thr Leu
            20                  25                  30

Ile Val Ile Arg Gly His Val Pro Ser Asp Ala Asp Arg Phe Gln Val
                35                  40                  45

Asp Leu Gln Asn Gly Ser Ser Met Lys Pro Arg Ala Asp Val Ala Phe
    50                  55                  60

His Phe Asn Pro Arg Phe Lys Arg Ala Gly Cys Ile Val Cys Asn Thr
65                  70                  75                  80

Leu Ile Asn Glu Lys Trp Gly Arg Glu Ile Thr Tyr Asp Thr Pro
                85                  90                  95

Phe Gln Lys Glu Lys Ser Phe Glu Ile Val Ile Met Val Leu Lys
            100                 105                 110

Ala Lys Pro Gln Val Ala Val Asn Gly Lys His Thr Leu Leu Tyr Gly
        115                 120                 125

His Arg Ile Gly Pro Glu Lys Ile Asp Thr Leu Gly Ile Tyr Gly Lys
    130                 135                 140

Val Asn Ile His Ser Ile Gly Pro Ser Pro Ser Asp Leu Gln Ser
145                 150                 155                 160

Thr Gln Ala Ser Ser Leu Glu Leu Thr Glu Ile Ser Arg Glu Asn Val
                165                 170                 175

Pro Lys Ser Gly Thr Pro Gln Leu Arg Leu Pro Phe Ala Ala Arg Leu
            180                 185                 190

Asn Thr Pro Met Gly Pro Gly Arg Thr Val Val Lys Gly Glu Val
                195                 200                 205

Asn Ala Asn Ala Lys Ser Pro Asn Val Asp Leu Leu Ala Gly Lys Ser
    210                 215                 220

Lys Asp Ile Ala Leu His Leu Asn Pro Arg Leu Asn Ile Lys Ala Phe
225                 230                 235                 240

Val Arg Asn Ser Phe Leu Gln Glu Ser Trp Gly Glu Glu Arg Asn
                245                 250                 255

Ile Thr Ser Phe Pro Phe Ser Pro Gly Met Tyr Phe Glu Met Ile Ile
            260                 265                 270

Tyr Cys Asp Val Arg Glu Phe Lys Val Ala Val Asn Gly Val His Ser
        275                 280                 285

Leu Glu Tyr Lys His Arg Phe Lys Glu Leu Ser Ser Ile Asp Thr Leu
    290                 295                 300

Glu Ile Asn Gly Asp Ile His Leu Leu Glu Val Arg Ser Trp
305                 310                 315
```

<210> SEQ ID NO 5
<211> LENGTH: 90
<212> TYPE: DNA
<213> ORGANISM: Artificial sequence
<220> FEATURE:
<223> OTHER INFORMATION: Oligonucleotide

<400> SEQUENCE: 5

```
tttagcttca gctcggactt acaaagtacc caagcatcta gtctggaact gacagagata      60
agtagagaaa atgttccaaa gtctggcacg                                      90
```